(12) United States Patent
Tsuchiya et al.

(10) Patent No.: US 10,888,448 B2
(45) Date of Patent: Jan. 12, 2021

(54) SUPPORTER

(71) Applicants: KOWA COMPANY, LTD., Nagoya (JP); ADVANCING INC., Osaka (JP); DMCHAIN COOPERATIVE, Kahoku (JP)

(72) Inventors: Akiharu Tsuchiya, Chuo-ku (JP); Hitoshi Ojima, Osaka (JP); Hidenori Kaseno, Kahoku (JP)

(73) Assignees: KOWA COMPANY, LTD., Nagoya (JP); ADVANCING INC., Osaka (JP); DMCHAIN COOPERATIVE, Kahoku (JP)

( * ) Notice: Subject to any disclaimer, the term of this patent is extended or adjusted under 35 U.S.C. 154(b) by 823 days.

(21) Appl. No.: 15/322,927

(22) PCT Filed: Jul. 1, 2015

(86) PCT No.: PCT/JP2015/069012
§ 371 (c)(1),
(2) Date: Dec. 29, 2016

(87) PCT Pub. No.: WO2016/002843
PCT Pub. Date: Jan. 7, 2016

(65) Prior Publication Data
US 2017/0135842 A1 May 18, 2017

(30) Foreign Application Priority Data
Jul. 1, 2014 (JP) .................................. 2014-136072

(51) Int. Cl.
*A61F 5/03* (2006.01)
*A61F 5/02* (2006.01)

(52) U.S. Cl.
CPC ................ *A61F 5/028* (2013.01); *A61F 5/02* (2013.01)

(58) Field of Classification Search
CPC .... A61F 5/02; A61F 5/028; A61F 5/03; A61F 5/022; A41D 13/0531
(Continued)

(56) References Cited

U.S. PATENT DOCUMENTS 1,604,076 A * 10/1926 Risselt ...................... A61F 5/03
450/123
2,104,699 A * 1/1938 O'Dell .................... A61F 5/028
602/19
(Continued)

FOREIGN PATENT DOCUMENTS

JP 6-142126 A 5/1994
JP 3146163 U 11/2008
(Continued)

OTHER PUBLICATIONS

International Search Report dated Sep. 15, 2015 in PCT/JP2015/069012 filed Jul. 1, 2015.

*Primary Examiner* — Rachael E Bredefeld
*Assistant Examiner* — Camtu T Nguyen
(74) *Attorney, Agent, or Firm* — Oblon, McClelland, Maier & Neustadt, L.L.P.

(57) ABSTRACT

Provided is a supporter in which it is possible to prevent floating of the supporter from the back portion of a wearer of the supporter in an upper side and a lower side of a back-contact section having a wide width and reliably support the waist portion of the wearer. The supporter 100 comprises: a band-shaped body section 10 provided with a back-contact section 11 which is brought into contact with the back portion of a wearer, and protruding sections 12 protruding to the right and left from both sides of the back-contact section 11; a pair of right and left auxiliary band sections 31 and 32 fixed so as to intersect one another in the vicinity of an upper side 11*a* of the back-contact section 11; a pair of right and left adjustment band sections (Continued)

51 and 52 loosely inserted into annular rings 41 and 42 respectively disposed at the auxiliary band sections 31 and 32; and a band-shaped support band section 70 fixed to the vicinity of a lower side 11b of the back-contact section 11.

20 Claims, 10 Drawing Sheets

(58) Field of Classification Search
USPC .................................................. D24/190–192
See application file for complete search history.

(56) References Cited

U.S. PATENT DOCUMENTS

| | | | | |
|---|---|---|---|---|
| 2,117,309 A | * | 5/1938 | Fritsch | A61F 5/03 602/19 |
| 2,476,029 A | * | 7/1949 | Dawson | A41C 1/08 450/138 |
| 3,096,760 A | * | 7/1963 | Nelkin | A61F 5/028 128/95.1 |
| 3,927,665 A | * | 12/1975 | Wax | A61F 5/028 602/19 |
| 4,135,503 A | * | 1/1979 | Romano | A61F 5/028 128/118.1 |
| 4,833,730 A | * | 5/1989 | Nelson | A61F 5/028 2/44 |
| 5,188,586 A | * | 2/1993 | Castel | A61F 5/028 128/845 |
| 5,195,948 A | * | 3/1993 | Hill | A61F 5/028 602/19 |
| 5,591,122 A | * | 1/1997 | Yewer, Jr. | A61F 5/028 128/100.1 |
| 5,776,087 A | * | 7/1998 | Nelson | A61F 5/028 2/255 |
| 5,820,575 A | * | 10/1998 | Cabrera | A61F 5/028 602/19 |
| 5,833,638 A | * | 11/1998 | Nelson | A61F 5/028 602/19 |
| 5,984,885 A | * | 11/1999 | Gaylord, Jr. | A61F 5/028 128/96.1 |
| 10,335,306 B2 | * | 7/2019 | Okada | A61F 5/024 |
| 2008/0268749 A1 | * | 10/2008 | Oyama | A41B 9/001 450/99 |
| 2014/0288474 A1 | | 9/2014 | Okada et al. | |

FOREIGN PATENT DOCUMENTS

| | | |
|---|---|---|
| WO | 2013/085027 A2 | 6/2013 |
| WO | WO 2013/085027 A2 * | 6/2013 |

* cited by examiner

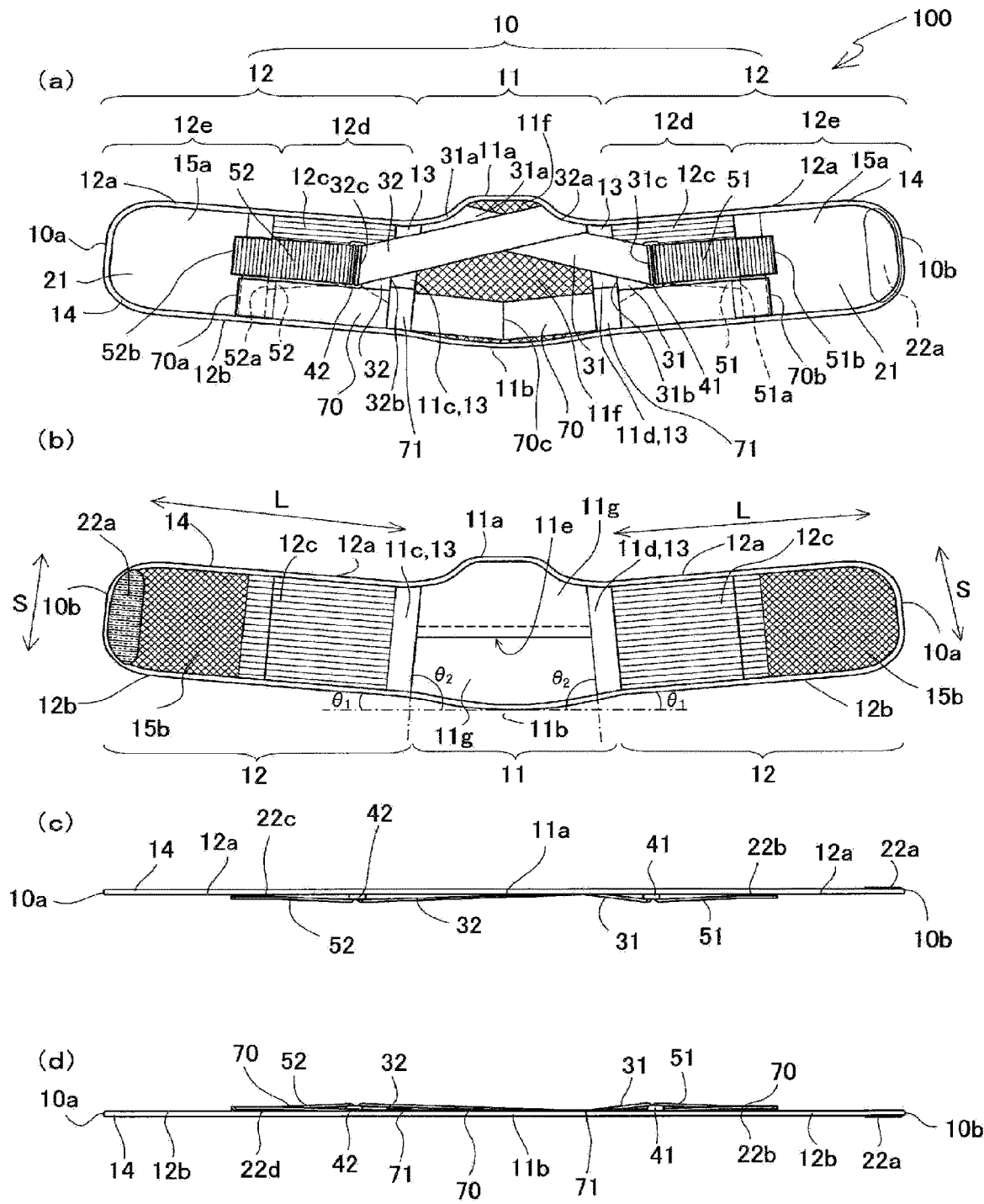
[FIG. 1]

[FIG. 2]
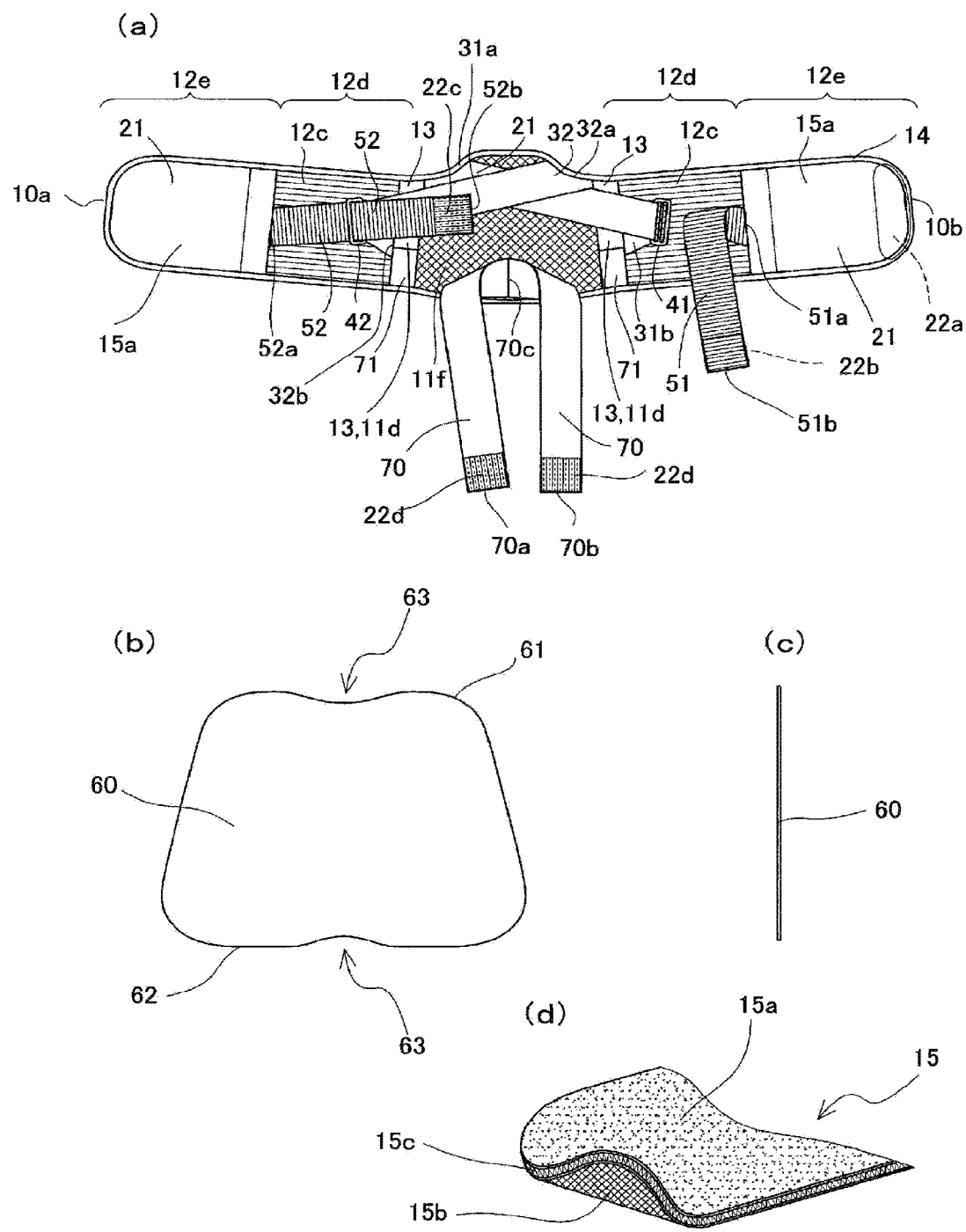

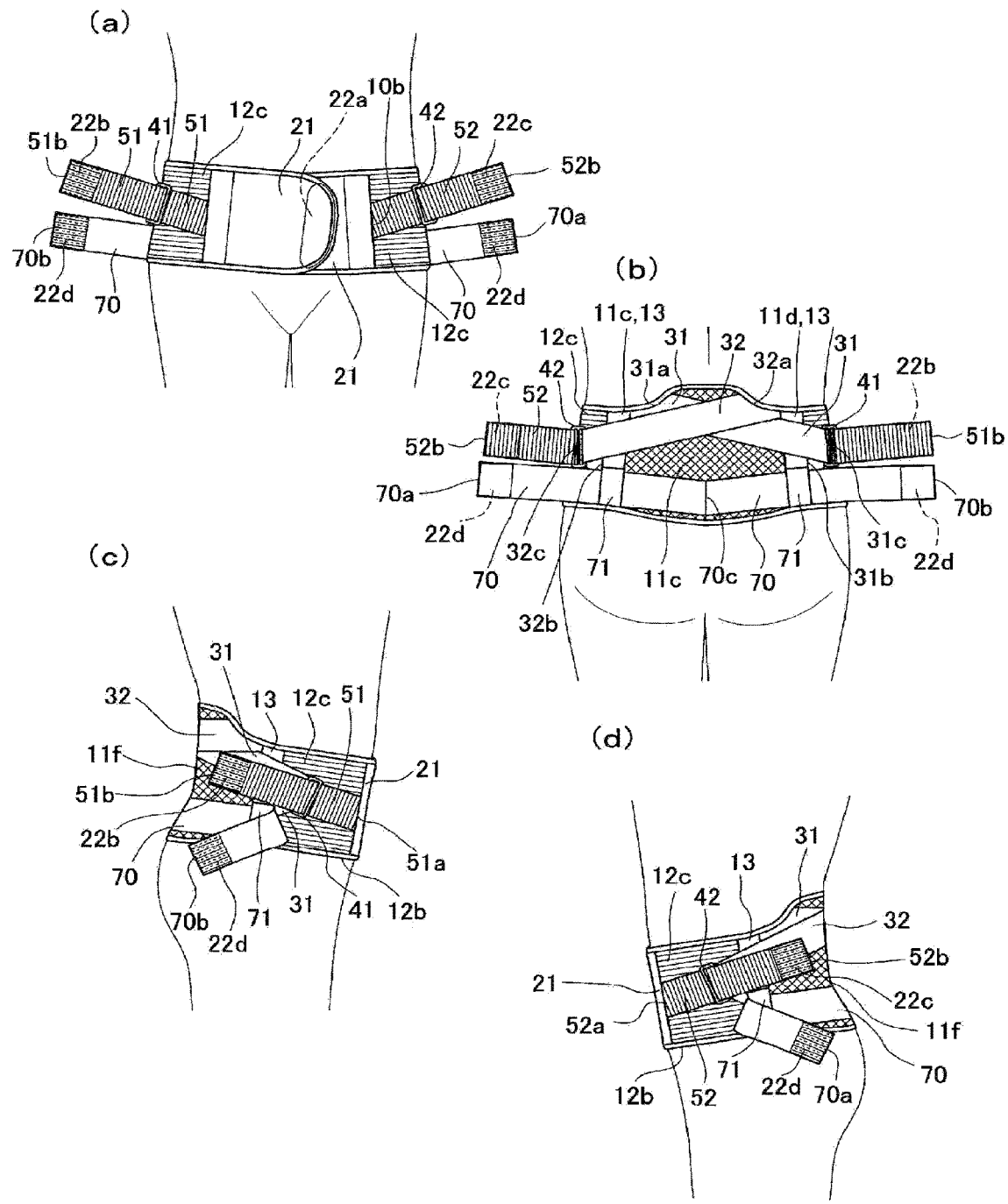
[FIG. 3]

[FIG. 4]
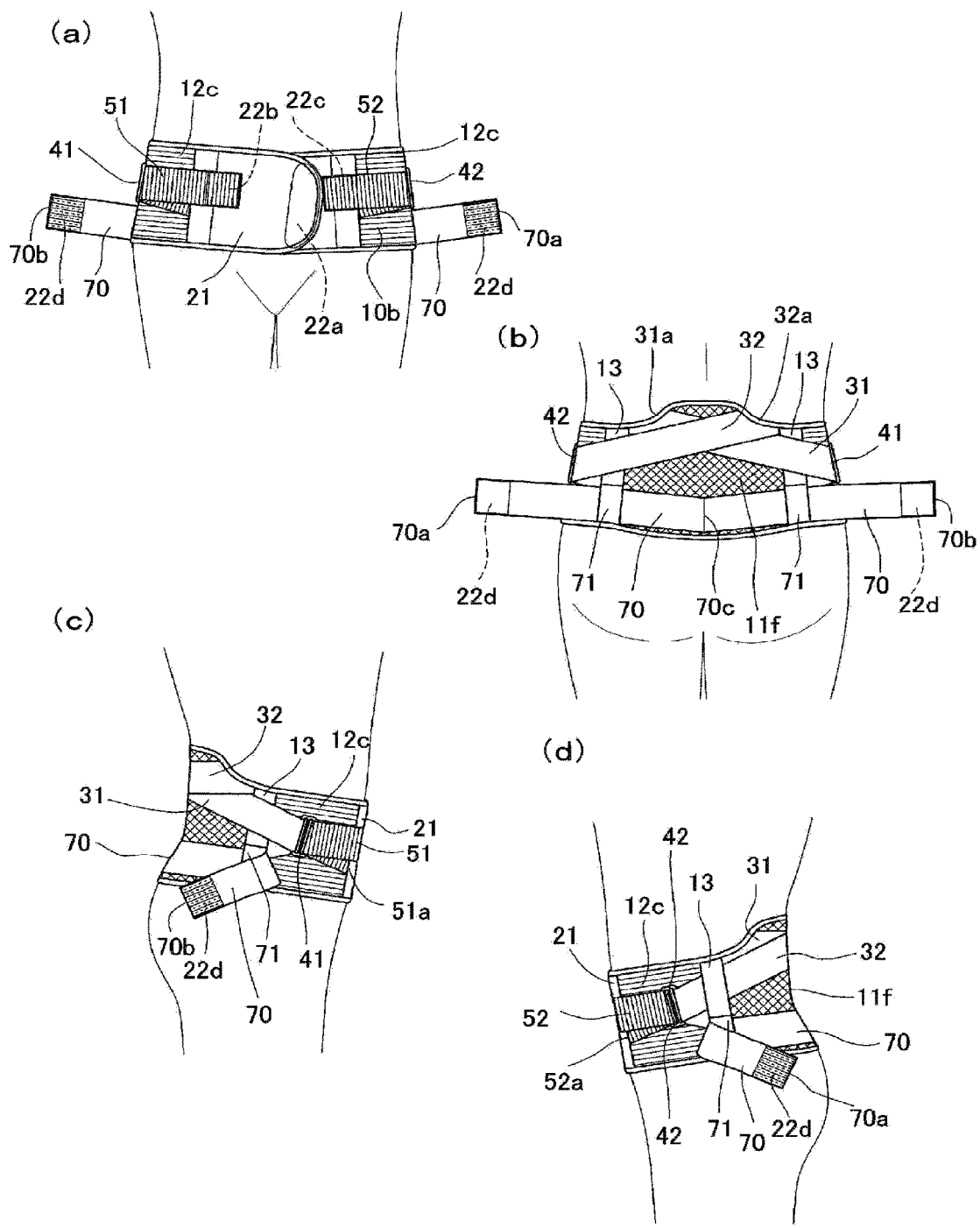

[FIG. 5]
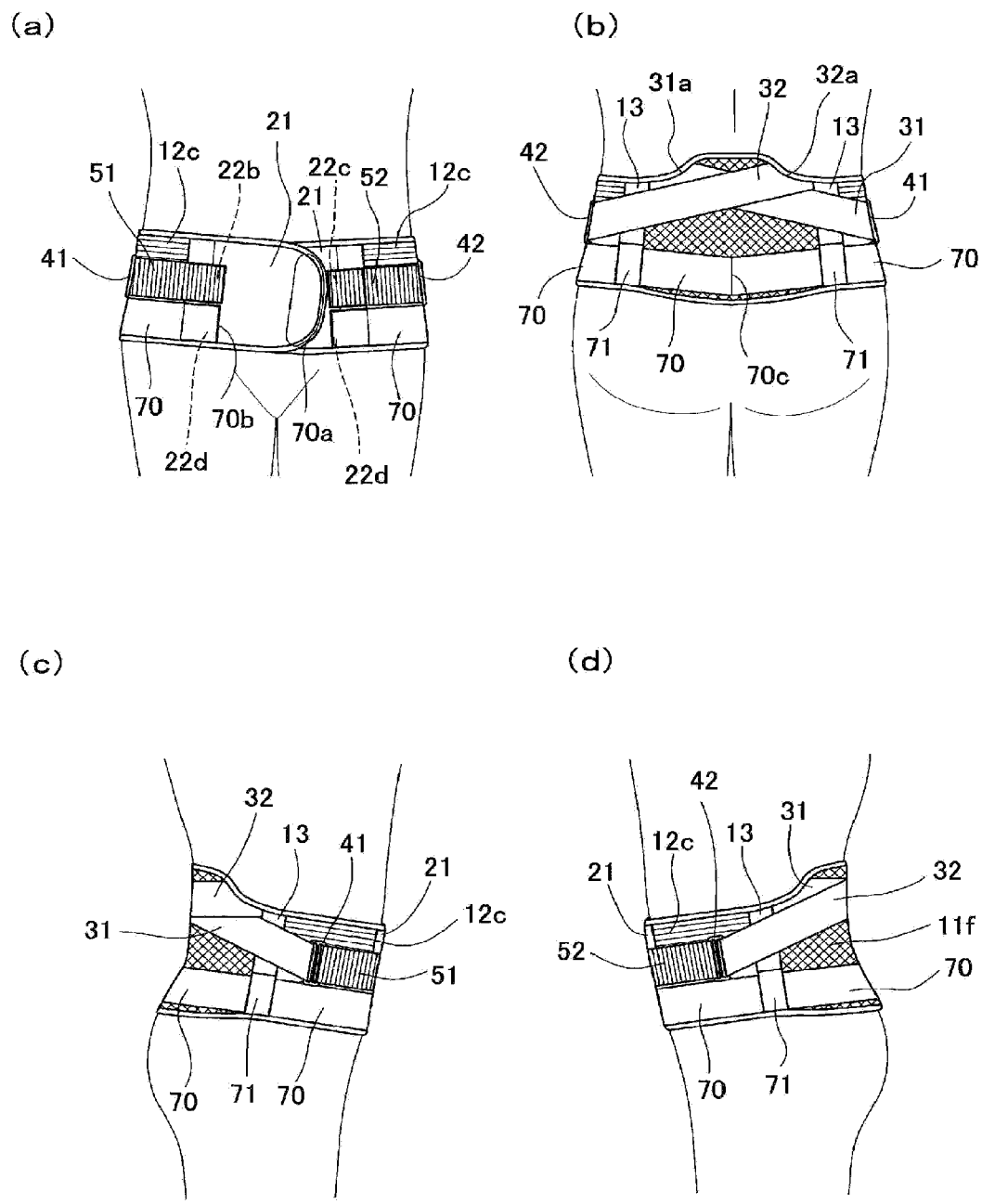

[FIG. 6]
(a)
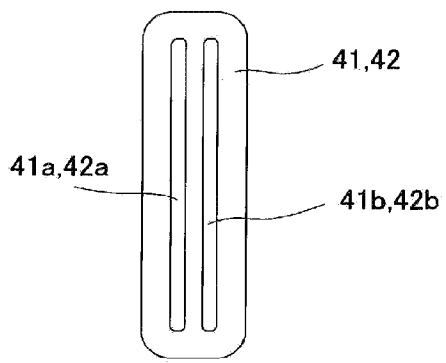
(b)
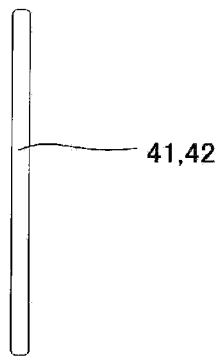
(c)
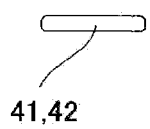
(d)
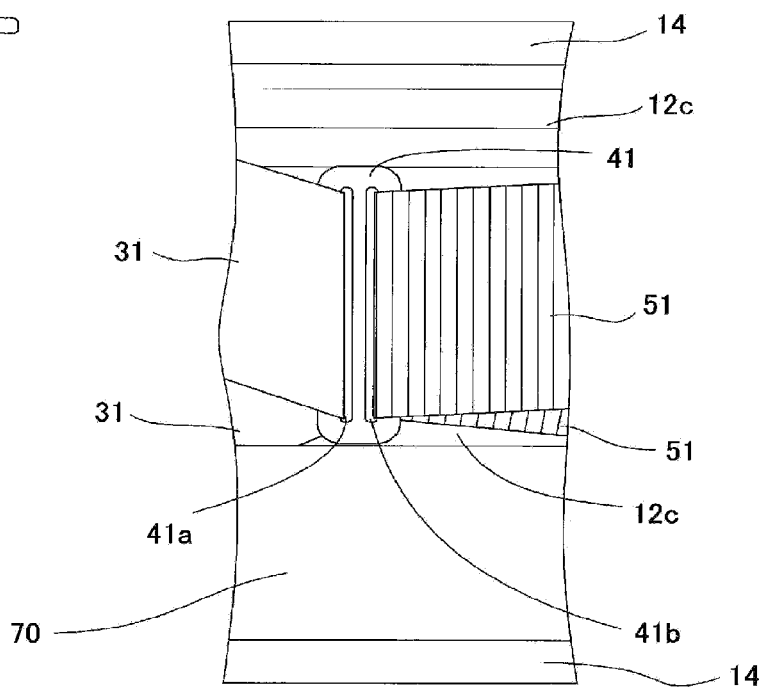
(e)
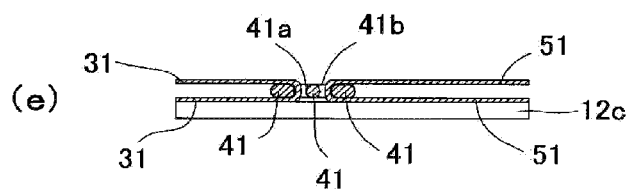

[FIG. 7]
(a)
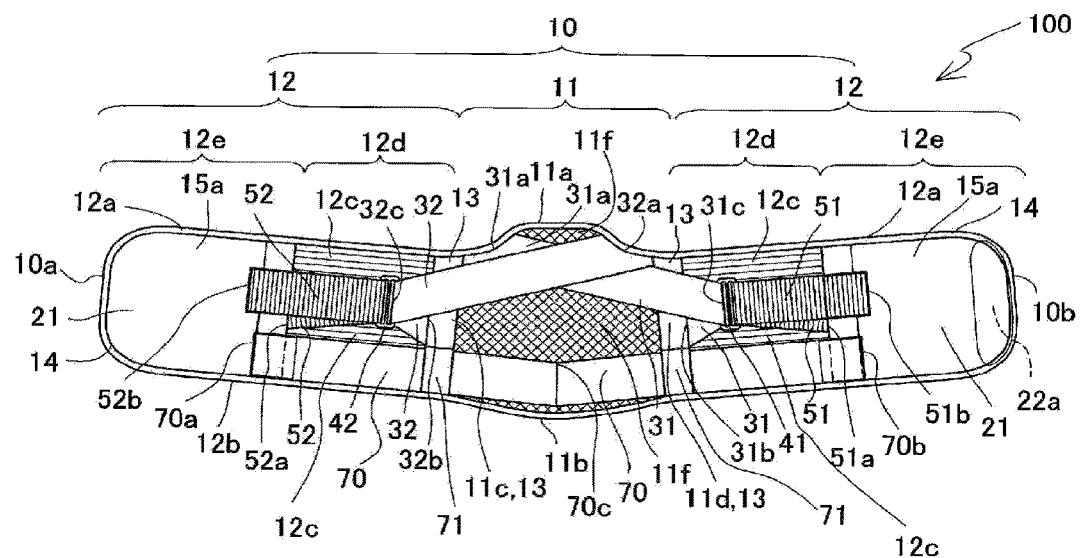
(b)
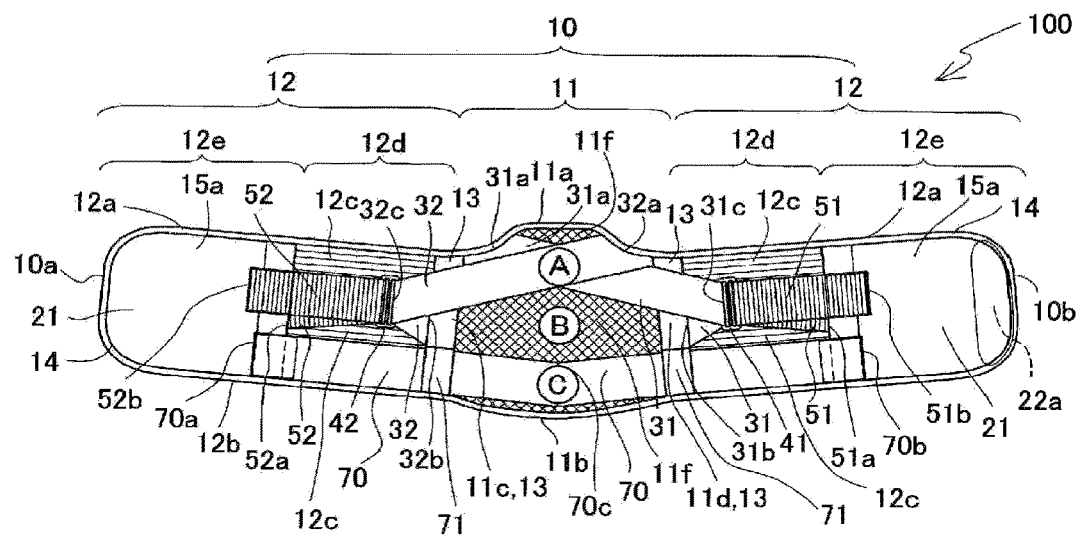

[FIG. 8]
(a)
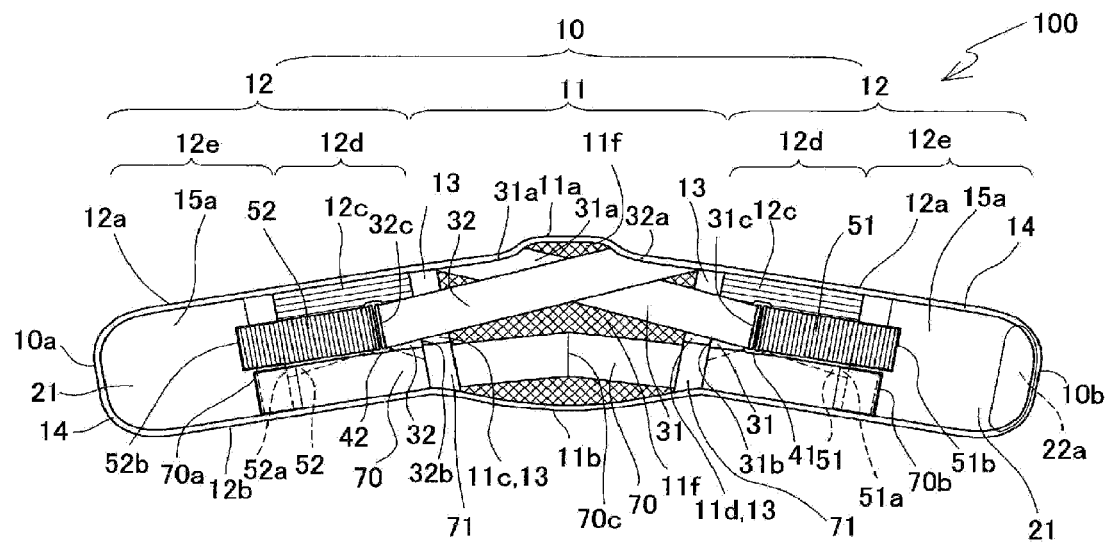
(b)
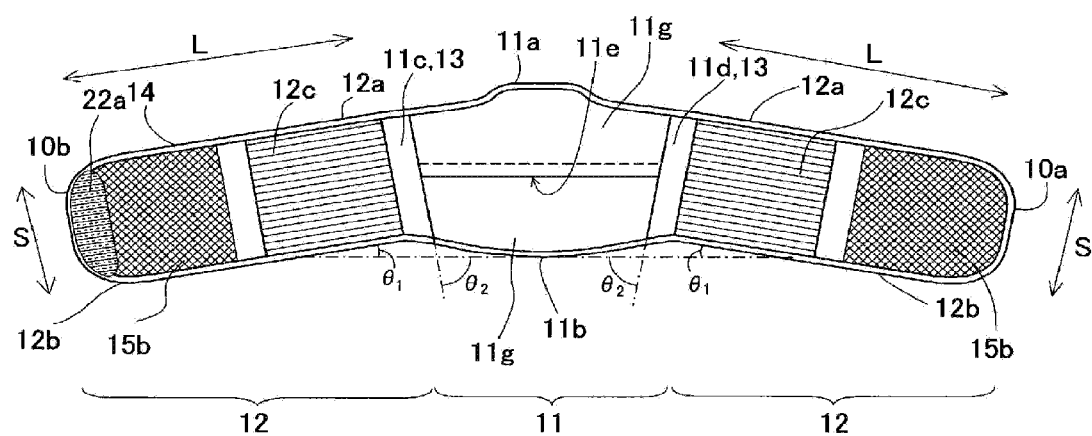

[FIG. 9]
(a)
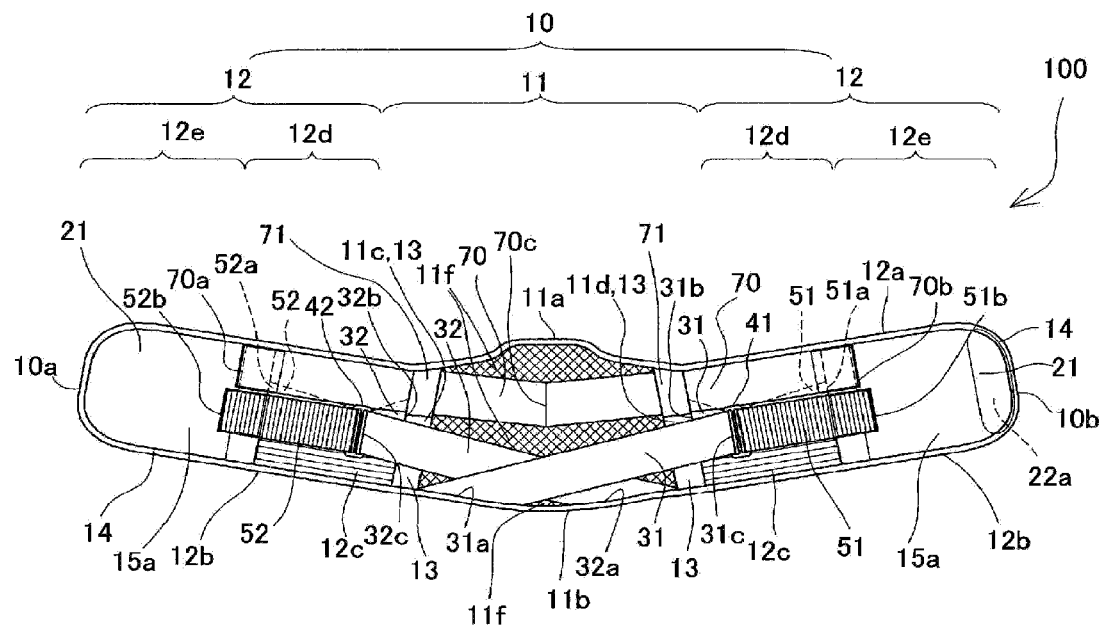
(b)
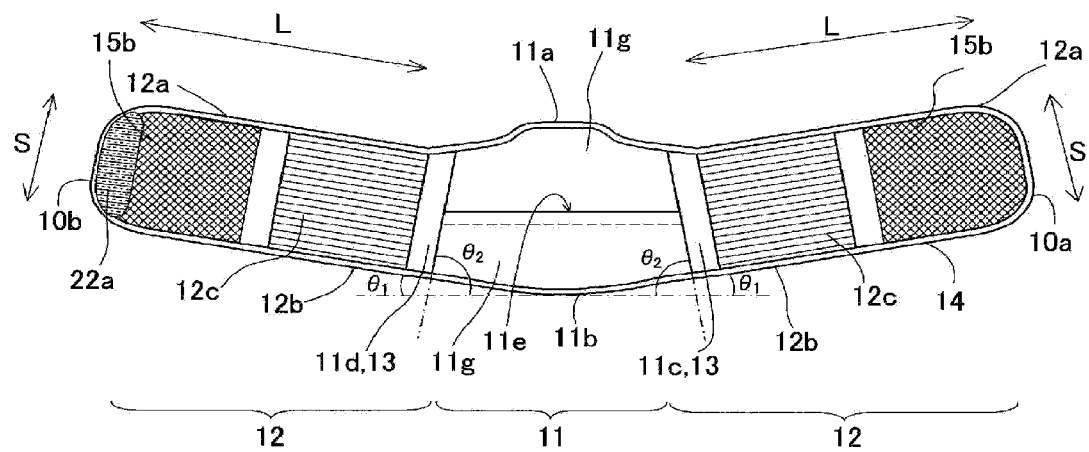

[FIG. 10]
(a)
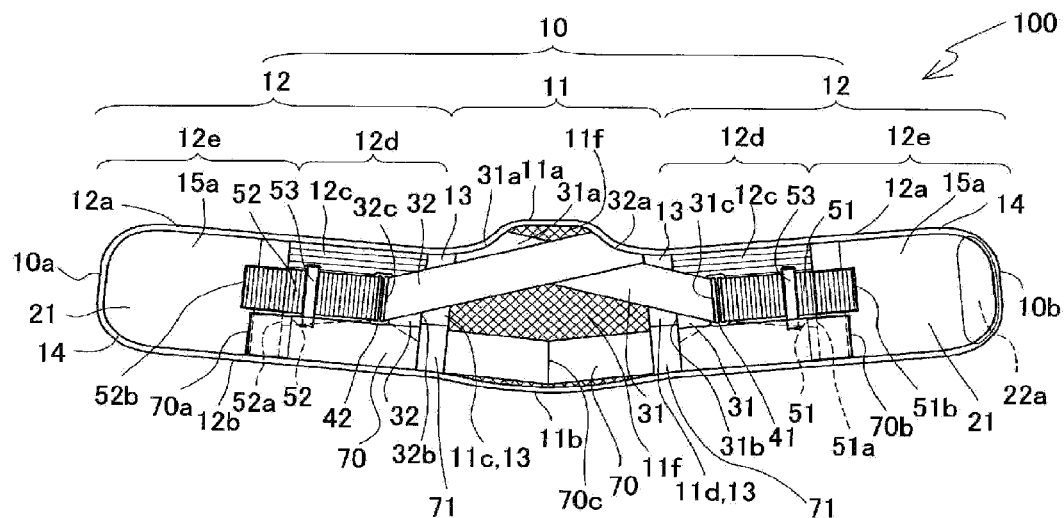
(b)
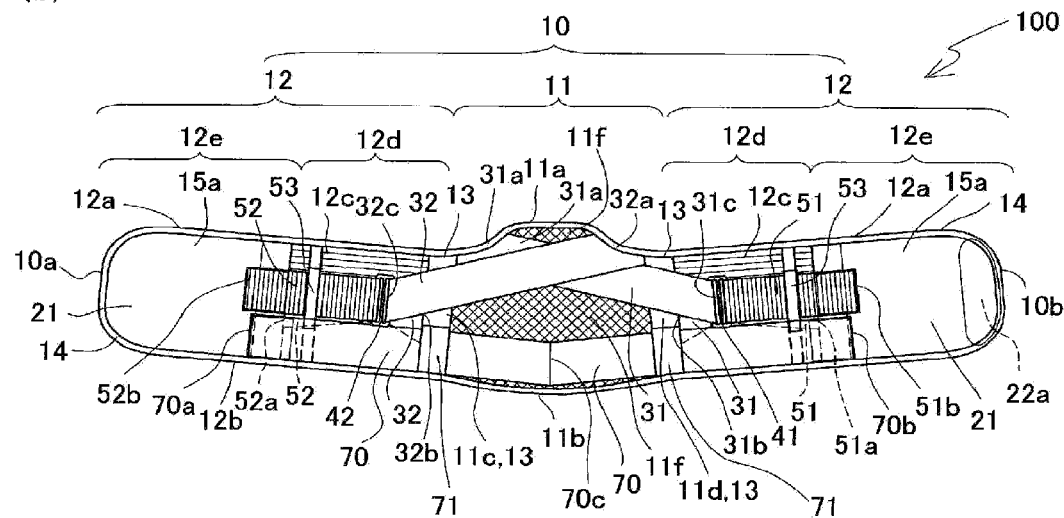

SUPPORTER

TECHNICAL FIELD

The present invention relates to a supporter capable of supporting a wearer's daily motion, and particularly, to a supporter capable of supporting the entire waist portion of a wearer including the pelvis of the wearer.

BACKGROUND ART

In a belt which supports the waist portion and the pelvis, of the related art, in a main body belt having a width which covers the waist portion and the pelvis portion, hook-and-loop fasteners for mounting and dismounting are provided at both right and left end portions of the main body belt, and the belt can be wound and mounted by adjusting tightening on the abdomen side of a wearer, and a belt for the waist portion and a belt for the pelvis, the tightening forces of which can be individually adjusted, are provided in parallel on the inner surface side of the main body belt, whereby the waist portion and the pelvis are supported at the same time by the belt for the waist portion and the belt for the pelvis provided in the main body belt (refer to, for example, PTL 1).

Further, in a lumbago band of the related art, a fixed plate formed by curing a forming material with a flexible base fabric impregnated with water-curable resin so as to correspond to the shape of the waist portion is joined to an abdominal bandage by belts (refer to, for example, PTL 2).

Further, a supporter of the related art is provided with: a body section having a back-contact section; loops disposed on the front surfaces of both ends of the body section; a first auxiliary band section which is fixed, at one end thereof, to an upper end of a left side of the back-contact section and, at the other end thereof, to a lower end of a right side of the back-contact section; a second auxiliary band section which is paired with the first auxiliary band section; a first ring which is disposed so as to be slidable between one end and the other end of the first auxiliary band section; a second ring which is paired with the first ring; a first adjustment band section having one end fixed to the loops on the right end side of the body section, and the other end capable of being engaged with the loops on the right end side of the body section; and a second adjustment band section which is paired with the first adjustment band section (refer to, for example, PTL 3).

CITATION LIST

Patent Literature

[PTL 1] Japanese Registered Utility Model No. 3146163
[PTL 2] JP-A-6-142126
[PTL 3] Pamphlet of International Publication No. 2013/085027

SUMMARY OF INVENTION

Technical Problem

In the belt (the lumbago band) which supports the waist portion and the pelvis, of the related art, the belt for the waist portion (an upper belt) and the belt for the pelvis (a lower belt) are provided in parallel on a back part (the fixed plate), whereby the belt for the waist portion (the upper belt) presses the slightly upper side of the center of the back part (the fixed plate) and the belt for the pelvis (the lower belt) presses the slightly lower side of the center of the back part (the fixed plate).

In contrast, the back portion of a wearer is curved, and therefore, in a structure in which the belt for the waist portion (the upper belt) and the belt for the pelvis (the lower belt) equally press upper and lower portions closer to the center of the back part (the fixed plate), like the belt (the lumbago band) which supports the waist portion and the pelvis, of the related art, floating of the back part (the fixed plate) from the back portion of the wearer occurs on the side of an upper side of the back part (the fixed plate), and thus there is a problem in which it is not possible to sufficiently support the waist portion of the wearer.

Further, in the supporter of the related art, in a case where the vertical width of the back-contact section is increased in accordance with the body type of a wearer, unless the widths of the first auxiliary band section and the second auxiliary band section are increased, the overlap areas of the first auxiliary band section and the second auxiliary band section with respect to the back-contact section become narrow, and thus there is a problem in which the effect of pressing the back-contact section by the first auxiliary band section and the second auxiliary band section cannot be sufficiently obtained.

Further, in the supporter of the related art, in a case where the vertical width of the back-contact section is increased in accordance with the body type of a wearer, in the structure in which one end of each of the first auxiliary band section and the second auxiliary band section is fixed to the upper end of the back-contact section and the other end of each of the first auxiliary band section and the second auxiliary band section is fixed to the lower end of the back-contact section, since the distance between the upper end and the lower end of the back-contact section is wide, pressing forces by the first auxiliary band section and the second auxiliary band section are not sufficiently applied to the center of the back-contact section, and thus there is a problem in which the supporting force of the back-contact section with respect to the waist portion of a wearer is lowered.

Further, in the supporter of the related art, in a case where the vertical width of the back-contact section is increased in accordance with the body type of a wearer, an intersection position of the first auxiliary band section and the second auxiliary band section moves from the upper side of the back-contact section, thereby becoming closer to the center of the back-contact section, and thus there is a possibility that floating of the back-contact section of the back portion of the wearer may occur on the side of the upper side of the back-contact section, and a new problem in which it is not possible to sufficiently support the waist portion of the wearer occurs.

The present invention has been made to solve the problems as described above and has an object to provide a supporter in which even in a back-contact section having a wide width, it is possible to prevent floating of the supporter from the back portion of a wearer in an upper side and reliably support the waist portion of the wearer.

Solution to Problem

According to the present invention, there is provided a supporter comprising: a back-contact section which is brought into contact with the back portion of a wearer; protruding sections which are disposed on both sides of the back-contact section, and in each of which a stretchable portion having stretchability in a longitudinal direction is disposed in contact with the back-contact section; a pair of auxiliary band sections which includes two band-shaped members having stretchability in a longitudinal direction, and in which both ends are fixed such that the two band-shaped members intersect one another on the back-contact section, and an annular ring is slidably disposed at each of the band-shaped members; a pair of adjustment band sections which includes two band-shaped members having stretchability lower than the stretchability of the auxiliary band sections, and each of which is loosely inserted into the annular ring disposed at each of the auxiliary band sections, and in each of which one end is fixed to a portion except for the stretchable portion of each of the right and left protruding sections and hooks of a hook-and-loop fastener is disposed at the other end; and a band-shaped support band section which includes a band-shaped member having stretchability in a longitudinal direction and is fixed to the back-contact section, and in which hooks of a hook-and-loop fastener is disposed at each of both end portions.

Advantageous Effects of Invention

In the supporters according to the present invention, even in a back-contact section having a wide width, floating of the supporter from the back portion of a wearer in an upper side and a lower side is prevented, and by applying relative importance to the pressing force from each band section in the upper side and the lower side of the back-contact section, it is possible to provide an optimal supporter according to the type of a lumbago.

BRIEF DESCRIPTION OF DRAWINGS

FIG. 1(a) is a diagram showing the front surface of a supporter according to a first embodiment, FIG. 1(b) is a diagram showing the lining surface of the supporter shown in FIG. 1(a), FIG. 1(c) is an upper side view of the supporter shown in FIG. 1(a), and FIG. 1(d) is a lower side view of the supporter shown in FIG. 1(a).

FIG. 2(a) is a diagram showing the front surface in a state where engagement of a first adjustment band section, a second adjustment band section, and a support band section of the supporter shown in FIG. 1(a) is released, the first adjustment band section is removed from a first ring, and the support band section is removed from a first guide part, FIG. 2(b) is a front view and a back view of a pressing section capable of being accommodated in a back-contact section of the supporter shown in FIG. 1(b), FIG. 2(c) is a left side view and a right side view of the pressing section shown in FIG. 2(b), and FIG. 2(d) is a perspective view for describing a double raschel knitted fabric which is used for a non-stretchable portion of the supporter shown in FIG. 1.

FIG. 3(a) is a front view for describing a method of wearing the supporter shown in FIG. 1, FIG. 3(b) is a back view for describing the method of wearing the supporter shown in FIG. 1, FIG. 3(c) is a right side view for describing the method of wearing the supporter shown in FIG. 1, and FIG. 3(d) is a left side view for describing the method of wearing the supporter shown in FIG. 1.

FIG. 4(a) is a front view for describing the continuation of the supporter wearing method shown in FIG. 3, FIG. 4(b) is a back view for describing the continuation of the supporter wearing method shown in FIG. 3, FIG. 4(c) is a right side view for describing the continuation of the supporter wearing method shown in FIG. 3, and FIG. 4(d) is a left side view for describing the continuation of the supporter wearing method shown in FIG. 3.

FIG. 5(a) is a front view for describing the continuation of the supporter wearing method shown in FIG. 4, FIG. 5(b) is a back view for describing the continuation of the supporter wearing method shown in FIG. 4, FIG. 5(c) is a right side view for describing the continuation of the supporter wearing method shown in FIG. 4, and FIG. 5(d) is a left side view for describing the continuation of the supporter wearing method shown in FIG. 4.

FIG. 6(a) is a front view and a back view showing a first ring and a second ring of the supporter shown in FIG. 1, FIG. 6(b) is a right side view and a left side view of the first ring and the second ring shown in FIG. 6(a), FIG. 6(c) is a plan view and a bottom view of the first ring and the second ring shown in FIG. 6(a), FIG. 6(d) is a partially enlarged view of the vicinity of the first ring shown in FIG. 5(c), and FIG. 6(e) is a central cross-sectional view in the partially enlarged view shown in FIG. 6(d).

FIG. 7(a) is a diagram showing the front surface of another supporter according to the first embodiment, and FIG. 7(b) is an explanatory diagram for describing a difference between pressing forces to the back-contact section shown in FIG. 7(a).

FIG. 8(a) is a diagram showing the front surface of still another supporter according to the first embodiment, and FIG. 8(b) is a diagram showing the lining surface of the supporter shown in FIG. 8(a).

FIG. 9(a) is a diagram showing the front surface of a supporter according to a second embodiment, and FIG. 9(b) is a diagram showing the lining surface of the supporter shown in FIG. 9(a).

FIG. 10(a) is a diagram showing the front surface of a supporter according to a third embodiment, and FIG. 10(b) is a diagram showing the front surface of another supporter according to the third embodiment.

DESCRIPTION OF EMBODIMENTS

First Embodiment of the Present Invention

A supporter 100 is used as a supporter (a corset) for the waist (in particular, for the pelvis) and roughly comprises a body section 10, a pair of right and left first and second auxiliary band sections 31 and 32, a pair of right and left first and second rings 41 and 42, a pair of right and left first and second adjustment band sections 51 and 52, and a support band section 70, as shown in FIGS. 1 and 2.

The body section 10 is composed of a band-shaped member and is provided with a back-contact section 11 which is disposed at a central portion of the approximately center of the band-shaped member and brought into contact with the back portion of a wearer, and protruding sections 12 which are disposed at both end portions on both sides of the back-contact section 11 and protrude upward with an upper side 12a and a lower side 12b of each of both end portions of the body section 10 being substantially parallel to each other and with an angle (on the acute angle side) between a horizontal portion of a lower side 11b of the back-contact section 11 and each of the upper side 12a and the lower side 12b being $\theta_1$ (for example, $\theta_1$ is in a range of 12° to 14°). Further, the body section 10 has a planar shape which is line-symmetric with a line segment connecting the midpoint of an upper side 11a and the midpoint of the lower side 11b of the back-contact section 11 as the axis of symmetry, and is circled around the waist portion of a wearer with the lining surface (refer to FIG. 1(b)) brought into contact with the waist portion.

The back-contact section 11 and the protruding section 12 are connected by sandwiching them between grosgrain tapes 13, each of which is woven using a polyester yarn by a needle loom, from the front surface and the lining surface of the body section 10, and sewing edge portions of the grosgrain tapes 13.

Further, inner layers which are sandwiched between the grosgrain tapes 13 from the front surface and the lining surface of the body section 10 are flattened without overlapping of a material of the back-contact section 11 and a material of the protruding section 12, whereby the thinning of the supporter 100 is attained and a neat feeling of wearing is realized, and even if a layering is performed on the supporter 100, it hardly affects an outerwear.

In particular, by sewing the materials of the back-contact section 11 and the protruding section 12 to each other by a zigzag stitch, it is possible to realize durability capable of withstanding even the harsh use of the supporter 100 while maintaining the thinness of the supporter 100.

Further, in the body section 10 according to this embodiment, edges (cut-off edges) of the back-contact section 11, the protruding section 12, and the grosgrain tape 13 are sewn (bound) with them gripped by a binder tape 14. However, fray prevention or decoration in the cut-off edges of the back-contact section 11, the protruding section 12, and grosgrain tape 13 may be carried out by edge sewing, bias bordering sewing, or the like. In particular, in the binding of the cut-off edge of the protruding section 12, since seams adjacent to each other are not dense due to sewing the binder tape 14 by a zigzag stitch, the stretchability in a longitudinal direction L of the protruding section 12 is not suppressed, and therefore, it is preferable.

The back-contact section 11 according to this embodiment has a substantially isosceles trapezoidal planar shape in which corner portions of both ends of the upper side 11*a* are curved so as to make the upper side 11*a* and the upper side 12*a* of the protruding section 12 continuous in an approximately S-shape, and an angle (on the acute angle side) $\theta_2$ between each of the opposite sides (a left side 11*c* and a right side 11*d*) which are not parallel to each other and the horizontal portion of the lower side 11*b* of the back-contact section 11 is $90°-\theta_1$ (for example, in a case where $\theta_1$ is in a range of 12° to 14°, $\theta_2$ is in a range of 76° to 78°). In particular, the back-contact section 11 according to this embodiment has a wide width (for example, in a range of 19 cm to 25 cm), thereby being able to reliably support the pelvis of a wearer to correspond to the size of the pelvis. Further, the back-contact section 11 may have a planar shape having a wide width with respect to the protruding section 12 by curving corner portions of both ends of the lower side 11*b* so as to make the lower side 11*b* and the lower side 12*b* of the protruding section 12 continuous in an approximately S-shape.

Further, the back-contact section 11 according to this embodiment is a bag-like body having an opening 11*e* in the lining surface and has a configuration in which a pressing section 60 made of a hard plate-like body which has high rigidity and does not have stretchability can be inserted into the bag-like body as a sock liner. However, if the back-contact section 11 does not have stretchability, it is not necessary to insert the pressing section 60 therein, and thus the back-contact section 11 does not also need to be a bag-like body.

The back-contact section 11 being made to be a bag-like body so as to enable insertion and removal of the pressing section 60 therein and therefrom is preferable, because it is possible to perform adjustment of the hardness of the back-contact section 11 by the presence or absence of the pressing section 60, a change in the material of the pressing section 60, or the like, and it is possible to launder the supporter 100 by removing the pressing section 60 from the back-contact section 11, and thereby it is hygienic.

Further, the back-contact section 11 being made to be a bag-like body is preferable, because it is possible to accommodate an accessory according to the needs of a wearer therein and it is possible to improve the convenience of the supporter 100, such as increasing the warmth of the supporter 100 by accommodating, for example, a pocket heater therein.

Further, in the back-contact section 11 according to this embodiment, a mesh material (a raschel mesh 11*f*) which is knitted using a nylon yarn by a double raschel warp knitting machine is used for a front fabric, whereby foreign matter such as fiber wastes accumulated in the bag-like body can be discharged to the outside through the knitted stitches, and thereby it is hygienic, and air permeability in the back-contact section 11 can be improved. Further, in the back-contact section 11 according to this embodiment, resin processing is applied to the finishing of the raschel mesh 11*f*, whereby the hardness of the warp knitted fabric is increased, and thus the supporting force of the supporter 100 with respect to the back portion of a wearer is strengthened.

Further, in the back-contact section 11 according to this embodiment, a crochet knitted material (a crochet-knitted fabric 11*g*) which is knitted using a polyurethane yarn and a heat-resistant polyester yarn by a crochet warp knitting machine is used for a back fabric, whereby the sense of touch is soft and a feeling against the back portion of a wearer is good, and by overlapping two crochet-knitted fabrics 11*g* at the opening 11*e*, it is possible to prevent an accessory such as a pocket heater accommodated in the bag-like body from coming out from the opening 11*e*.

Further, in the back-contact section 11 according to this embodiment, a warp knitted fabric to which resin processing is not applied is used as the back fabric, whereby even if the knitted fabric is cut, the knitting yarn does not become loose from the cut-off edge, and thus it is possible to process the knitted fabric into a free shape, and it is possible to provide desired stretchability to enable the insertion of an accessory into the bag-like body.

The warp knitting machine is classified roughly into a raschel warp knitting machine which forms a knitted fabric (a raschel knitted fabric) having a specialized pattern by using needles in various ways, and a tricot warp knitting machine which forms a knitted fabric (a tricot knitted fabric) specialized in high production rather than a pattern. Further, the raschel warp knitting machine is subdivided into a double raschel warp knitting machine, a Rasserina warp knitting machine, a lace warp knitting machine or a crochet warp knitting machine (a crochet knitting machine), and the like.

Further, the warp knitting creates a knitted fabric by creating knitted stitches in a longitudinal direction (a knitting direction) and combining the knitted stitches by using a large number of warps (warping yarns) arranged in parallel one by one.

As a combination method, there are various types. However, as a typical combination method, a method of creating a knitted fabric as a whole while mutually entangling warps adjacent to each other, or a method of forming a knitted fabric as a whole by creating a large number of independent chain stitches by each of warps and inserting another set of warps prepared separately into the chain stitches, thereby connecting the chain stitches in a transverse direction while collecting several chain stitches, can be given.

Further, the warp knitting has the features such as high productivity and a large knitted width, in addition to fray being difficult and elongation in the transverse direction (the direction perpendicular to the knitting direction) being small.

In the pressing section 60 according to this embodiment, a resin panel made of polypropylene (PP) having a melting point in a range of 150° C. to 160° C. and having more excellent heat resistance than a polyethylene material having a melting point in a range of 105° C. to 120° C. is used, whereby in a case where a pocket heater is accommodated in the back-contact section 11, it is possible to suppress the deformation of the pressing section 60 due to heat generation of the pocket heater.

Further, as shown in FIG. 2(b), the pressing section 60 according to this embodiment has a substantially isosceles trapezoidal planar shape conforming to the planar shape of the back-contact section 11, and has a shape in which four corner portions are rounded and a concave portion 63 is formed at the center of each of an upper bottom 61 and a lower bottom 62, whereby the pressing section 60 is easily twisted with a line segment connecting the midpoint of the upper bottom 61 and the midpoint of the lower bottom 62 as a basis, a repulsive force is generated against the twist, and an axopodium is assisted with respect to the movement of a wearer, thereby facilitating the walking of the wearer. Further, if it is a resin panel in which the concave portion 63 is not formed in the pressing section 60, in a case where the pressing section 60 is bent with the line segment connecting the midpoint of the upper bottom 61 and the midpoint of the lower bottom 62 as a basis, the center of the upper bottom 61 protrudes most highly, and a protruding portion of the pressing section 60 comes into contact with the back portion of a wearer, thereby causing pain, and therefore, it is preferable to form the concave portion 63 at the center of the upper bottom 61.

The protruding section 12 according to this embodiment is composed of an area having stretchability (hereinafter referred to as a stretchable portion 12d), which is disposed on each of both sides of the back-contact section 11, and an area having no stretchability (hereinafter referred to as a non-stretchable portion 12e), which is disposed adjacent to the stretchable portion 12d.

The stretchable portion 12d of the protruding section 12 is composed of a power net fabric 12c which is woven by a needle loom and in which in addition to a polyurethane yarn and a polyester yarn, a monofilament (single fiber) yarn made of nylon is woven in order to prevent folding of the fabric, and is a fabric in which stretchability in the longitudinal direction L is provided and stretchability in a short side direction S is suppressed. The stretchable portion 12d of the protruding section 12 has stretchability higher than the stretchability of the first auxiliary band section 31 and the second auxiliary band section 32 (described later).

In a case where normal monofilament yarns (for example, 600 deniers per piece) are used in the protruding section 12, since a single monofilament yarn is thick and is a warp like a wire, there is a concern that the tip of the monofilament yarn may protrude from a cut side, thereby piercing a wearer.

For this reason, in the stretchable portion 12d of the protruding section 12 according to this embodiment, gathered yarns (for example, 10 pieces) of monofilament yarns (for example, 50 deniers per piece) each having a low count is used, whereby the tip of the monofilament yarn is suppressed from protruding from the cut edge while a desired hardness and air permeability are maintained, and even if the monofilament yarn protrudes, since the thickness of a single monofilament is thin, the tip of the monofilament yarn does not pierce a wearer, and thus it is possible to reduce irritation to the skin of a wearer.

Further, in the stretchable portion 12d of the protruding section 12 according to this embodiment, resin processing having high resin concentration is applied to the finishing of the protruding section 12, thereby further increasing the hardness of the fabric, and thus the supporting force of the supporter 100 with respect to the anterior abdomen and the regio lateralis of a wearer is strengthened, and since the fabric itself has a mesh structure, air permeability is good.

Hook-and-loop fasteners (hooks or loops) are disposed at the front surfaces of both ends (a left end 10a and a right end 10b) of the body section 10 and the lining surface of the left end 10a or the right end 10b of the body section 10, and thus the different faces of the body section 10 are engaged with each other.

Further, in the body section 10 according to this embodiment, loops 21 of the hook-and-loop fastener is disposed on each of the sides of both ends (the left end 10a and the right end 10b) in the front surface of the supporter 100 shown in FIG. 1(a) and hooks 22a of the hook-and-loop fastener is disposed on the right end 10b side in the lining surface shown in FIG. 1(b).

In particular, a base material of the non-stretchable portion 12e of the protruding section 12 according to this embodiment is composed of a double raschel knitted fabric 15 which is knitted by a double raschel knitting machine and configured of a front knitted surface 15a having a loop structure, a back knitted surface 15b having a mesh structure, and a connection portion 15c having a double raschel structure, as shown in FIG. 2(d), and is a knitted fabric in which stretchability in the longitudinal direction L and the short side direction S is suppressed. That is, the non-stretchable portion 12e (the double raschel knitted fabric 15) according to this embodiment has a loop structure (the front knitted surface 15a), and therefore, the non-stretchable portion 12e corresponds to the loops 21 of the hook-and-loop fastener which is disposed on each of the sides of both ends (the left end 10a and the right end 10b) in the front surface of the supporter 100 shown in FIG. 1(a). Further, the non-stretchable portion 12e (the double raschel knitted fabric 15) according to this embodiment has a double raschel mesh structure (the back knitted surface 15b and the connection portion 15c), and therefore, the non-stretchable portion 12e has the most excellent air permeability, compared to the back-contact section 11 (the raschel mesh 11f and the crochet-knitted fabric 11g) and the stretchable portion 12d (the power net fabric 12c), and by disposing the non-stretchable portions 12e at overlapping areas of both ends of the body section 10 in the worn state of the supporter 100, it is possible to increase a feeling of wearing by securing the air permeability of the supporter 100.

In the supporter 100 according to this embodiment, the power net fabric 12c and the double raschel knitted fabric 15 are partially overlapped and sewn at a boundary portion, and the edges (the cut-off edges) of the power net fabric 12c and the loops 21 (the double raschel knitted fabric 15) of the hook-and-loop fastener are gripped by the binder tape 14 and sewn to each other.

Further, in the supporter 100 according to this embodiment, one end of the binder tape 14 is disposed at the right end 10b of the body section 10, the other end of the binder tape 14 circled around the body section 10 is disposed on the lining surface side of the body section 10, the other end of the binder tape 14 is sandwiched between the hooks 22a of the hook-and-loop fastener and the non-stretchable portion 12e (the double raschel knitted fabric 15) of the protruding section 12, and the other end of the binder tape 14 is sewn at the same time as the sewing of the hooks 22a to the non-stretchable portion 12e (the double raschel knitted fabric 15) of the protruding section 12. Due to this configuration, it is possible to simplify the manufacturing process of the supporter 100, and the other end of the binder tape 14 is suppressed from protruding from the surface of the supporter 100, whereby the beauty of the supporter 100 is not impaired.

The pair of right and left auxiliary band sections according to this embodiment is composed of two band-shaped members (the first auxiliary band section 31 and the second auxiliary band section 32) having stretchability in the longitudinal direction and is fixed such that the two band-shaped members intersect one another in the vicinity of the upper side 11a of the back-contact section 11.

The first auxiliary band section 31 is composed of a band-shaped member having stretchability in the longitudinal direction of the first auxiliary band section 31, one end 31a of the band-shaped member is fixed to one end of the upper side 11a of the back-contact section 11 and/or an upper end of one side (for example, the left side 11c) of the lateral sides of the back-contact section 11 in the front surface of the body section 10, the band-shaped member is folded back on the outside (the right side) of the back-contact section 11 when viewed in a planar view (refer to FIG. 1(a)) of the body section 10, and the other end 31b of the band-shaped member is fixed to the approximately center in the vicinity of the other side (for example, the right side 11d) of the lateral sides being in contact with the back-contact section 11 in the stretchable portion 12d of the protruding section 12 in the front surface of the body section 10. As long as the first auxiliary band section 31 and the second auxiliary band section 32 intersect one another in the vicinity of the upper side 11a of the back-contact section 11, the other end 31b of the first auxiliary band section 31 does not need to be fixed to the approximately center in the vicinity of the other side (for example, the right side 11d) of the lateral sides and may be fixed in contact with the lower end in the vicinity of the other side (for example, the right side 11d) of the lateral sides.

A portion of one end 31a of the first auxiliary band section 31 according to this embodiment is sewn with it sandwiched between the back-contact section 11 (the raschel mesh 11f) and the grosgrain tape 13 at one end of the upper side 11a (the upper end of the left side 11c) of the back-contact section 11, as shown in FIG. 1(a), and the remaining portion of one end 31a is sewn with it sandwiched between the back-contact section 11 (the raschel mesh 11f) and the binder tape 14. Further, the other end 31b of the first auxiliary band section 31 according to this embodiment is sewn with it sandwiched between the protruding section 12 (the power net fabric 12c) and the grosgrain tape 13 at the approximately center in the vicinity of the other side (the right side 11d) of the lateral sides of the back-contact section 11, as shown in FIGS. 1(a) and 2(a).

One end 31a of the first auxiliary band section 31 according to this embodiment is fixed to extend over one end of the upper side 11a of the back-contact section 11 and the upper end of one side (for example, the left side 11c) of the lateral sides of the back-contact section 11 in the front surface of the body section 10, as shown in FIG. 1(a). However, one end 31a may be fixed only to the upper side 11a of the back-contact section 11 in the front surface of the body section 10 and may be fixed only to one side (for example, the left side 11c) of the lateral sides of the back-contact section 11.

The second auxiliary band section 32 is composed of a band-shaped member having stretchability in the longitudinal direction of the second auxiliary band section 32, one end 32a of the band-shaped member is fixed to the other end of the upper side 11a of the back-contact section 11 and/or an upper end of the other side (for example, the right side 11d) of the lateral sides of the back-contact section 11 in the front surface of the body section 10, the band-shaped member is folded back on the outside (the left side) of the back-contact section 11 when viewed in a planar view (refer to FIG. 1(a)) of the body section 10, and the other end 32b of the band-shaped member is fixed to the approximately center in the vicinity of one side (for example, the left side 11c) of the lateral sides being in contact with the back-contact section 11 in the stretchable portion 12d of the protruding section 12 in the front surface of the body section 10, and the second auxiliary band section 32 is paired with the first auxiliary band section 31. As long as the first auxiliary band section 31 and the second auxiliary band section 32 intersect one another in the vicinity of the upper side 11a of the back-contact section 11, the other end 32b of the second auxiliary band section 32 does not need to be fixed to the approximately center in the vicinity of one side (for example, the left side 11c) of the lateral sides and may be fixed in contact with the lower end in the vicinity of one side (for example, the left side 11c) of the lateral sides.

As an intersection portion of the first auxiliary band section 31 and the second auxiliary band section 32, a configuration in which the second auxiliary band section 32 straddles the first auxiliary band section 31 is shown in FIGS. 1(a), 1(c), 1(d), 2(a), 3(b), 3(c), 3(d), 4(b), 4(c), 4(d), 5(b), 5(c), and 5(d). However, a configuration in which the first auxiliary band section 31 straddles the second auxiliary band section 32 is also acceptable.

A portion of one end 32a of the second auxiliary band section 32 according to this embodiment is sewn with it sandwiched between the back-contact section 11 (the raschel mesh 11f) and the grosgrain tape 13 at the other end of the upper side 11a (the upper end of the right side 11d) of the back-contact section 11, as shown in FIG. 1(a), and the remaining portion of one end 32a is sewn with it sandwiched between the back-contact section 11 (the raschel mesh 11f) and the binder tape 14. Further, the other end 32b of the second auxiliary band section 32 according to this embodiment is sewn with it sandwiched between the protruding section 12 (the power net fabric 12c) and the grosgrain tape 13 at the approximately center in the vicinity of one side (the left side 11c) of the lateral sides of the back-contact section 11, as shown in FIGS. 1(a) and 2(a).

One end 32a of the second auxiliary band section 32 according to this embodiment is fixed to extend over the other end of the upper side 11a of the back-contact section 11 and the upper end of the other side (for example, the right side 11d) of the lateral sides of the back-contact section 11 in the front surface of the body section 10, as shown in FIG. 1(a). However, one end 32a may be fixed only to the upper side 11a of the back-contact section 11 in the front surface of the body section 10 and may be fixed only to the other side (for example, the right side 11d) of the lateral sides of the back-contact section 11.

In each of the first auxiliary band section 31 and the second auxiliary band section 32 according to this embodiment, a rubber weave which is woven using a polyurethane yarn and a polyester yarn by a needle loom is used as a base material, and polyurethane is used as a material of an elastic fiber, and thereby, durability (heat resistance) is excellent, and an allergic reaction (a hypersensitivity reaction) that occurs in a case where raw rubber is used as a material of an elastic fiber is suppressed, and thus it is gentle to the skin of a wearer.

The first ring 41 has an annular shape and is disposed so as to be slidable between one end 31a and the other end 32b of the first auxiliary band section 31.

In particular, the first ring 41 according to this embodiment has two through-holes (a first long hole 41a and a second long hole 41b) which are provided in parallel to correspond to the widths and the thicknesses of the first auxiliary band section 31 and the first adjustment band section 51, as shown in FIGS. 6(a) to 6(c).

The through-hole corresponding to the width and the thickness of each of the first auxiliary band section 31 and the first adjustment band section 51 means a hole having a size in which there is no influence on the sliding of the first ring 41 and the band section (the first auxiliary band section 31 or the first adjustment band section 51) itself is not twisted in the through-hole (the first long hole 41a or the second long hole 41b).

The second ring 42 has an annular shape, is disposed so as to be slidable between one end 32a and the other end 32b of the second auxiliary band section 32, and is paired with the first ring 41.

In particular, the second ring 42 according to this embodiment has two through-holes (a first long hole 42a and a second long hole 42b) which are provided in parallel to correspond to the widths and the thicknesses of the second auxiliary band section 32 and the second adjustment band section 52, as shown in FIGS. 6(a) to 6(c).

The through-hole corresponding to the width and the thickness of each of the second auxiliary band section 32 and the second adjustment band section 52 means a hole having a size in which there is no influence on the sliding of the second ring 42 and the band section (the second auxiliary band section 32 or the second adjustment band section 52) itself is not twisted in the through-hole (the first long hole 42a or the second long hole 42b).

Each of the first ring 41 and the second ring 42 according to this embodiment is a flat can which is formed by a die forming machine, and has all of high hardness, flexibility, and heat resistance due to using polyacetal as a material.

Further, each of the first ring 41 and the second ring 42 according to this embodiment has a configuration having two through-holes (the first long hole 42a and the second long hole 42b). However, a configuration is also acceptable in which each of the first ring 41 and the second ring 42 has a single through-hole and the first auxiliary band section 31 (the second auxiliary band section 32) and the first adjustment band section 51 (the second adjustment band section 52) are inserted into the single through-hole.

The pair of right and left adjustment band sections according to this embodiment is composed of two band-shaped members (the first adjustment band section 51 and the second adjustment band section 52) having stretchability in the longitudinal direction.

The first adjustment band section 51 is loosely inserted into the first ring 41 and is composed of a band-shaped member having stretchability lower than the stretchability of the first auxiliary band section 31. One end 51a of the band-shaped member is fixed to the non-stretchable portion 12e of the protruding section 12 on the right end 10b side of the body section 10 in the front surface of the body section 10, the band-shaped member is inserted into the first ring 41 and folded back in the direction opposite to a folded portion (a bent portion 31c) of the first auxiliary band section 31 when viewed in a planar view (refer to FIG. 1(a)) of the body section 10, and the other end 51b of the band-shaped member can be engaged with a portion except for the stretchable portion 12d of the protruding section 12 on the right end 10b side of the body section 10 in the front surface of the body section 10.

In particular, one end 51a of the first adjustment band section 51 according to this embodiment is obliquely fixed to the approximately center of the non-stretchable portion 12e of the protruding section 12 on the right end 10b side of the body section 10 in the front surface of the body section 10 in a state where the other end 51b side faces toward the intersection portion of the first auxiliary band section 31 and the second auxiliary band section 32 with the approximately center of the non-stretchable portion 12e of the protruding section 12 on the right end 10b side of the body section 10 in the front surface of the body section 10 as a supporting point, in a flatly-laid state (refer to FIG. 2(a)) in which the engagement of the other end 51b of the first adjustment band section 51 is released.

Further, the fixed position of one end 51a and the engagement position of the other end 51b side of the first adjustment band section 51 are on the right end 10b side of the body section 10 with respect to the position (the bent portion 31c) farthest from one end 31a and the other end 31b of the first auxiliary band section 31, in the range of motion of the first ring 41 which is bound to the first auxiliary band section 31 having the natural length in the flatly-laid state (refer to FIG. 1(a)) of the supporter 100.

In the first adjustment band section 51 according to this embodiment, a PP tape which is woven using a polypropylene yarn and a polyester yarn by a needle loom is used as a base material, and one end 51a of the first adjustment band section 51 (the base material) is sandwiched between the stretchable portion 12d (the power net fabric 12c) and the non-stretchable portion 12e (the double raschel knitted fabric 15) of the protruding section 12 at the approximately center in the short side direction S of the protruding section 12 and one end 51a is sewn at the same time as the sewing of the stretchable portion 12d (the power net fabric 12c) and the non-stretchable portion 12e (the double raschel knitted fabric 15) of the protruding section 12.

Further, in the first adjustment band section 51 according to this embodiment, hooks 22b (refer to FIG. 2(a)) of a hook-and-loop fastener, which is engaged with the loops 21 of the hook-and-loop fastener on the right end 10b side of the body section 10, is disposed to be sewn to the surface facing the loops 21 of the hook-and-loop fastener on the right end 10b side of the body section 10, in the other end 51b of the first adjustment band section 51 (the base material).

Further, in the first adjustment band section 51 according to this embodiment, an end portion of the base material, which becomes the other end 51b, is folded back (a folded structure), and the hooks 22b of the hook-and-loop fastener is sewn to be superimposed on the folded-back portion (the folded structure), whereby the thickness of the other end 51b becomes thicker, and thus falling-off of the first adjustment band section 51 from the first ring 41 is prevented and a wearer can easily grip the other end 51b. Therefore, it is possible to obtain an easy-to-use supporters 100.

The second adjustment band section 52 is loosely inserted into the second ring 42 and is composed of a band-shaped member having stretchability lower than the stretchability of the second auxiliary band section 32. One end 52a of the band-shaped member is fixed to the non-stretchable portion 12e of the protruding section 12 on the left end 10a side of the body section 10 in the front surface of the body section 10, the band-shaped member is inserted into the second ring 42 and folded back in the direction opposite to a folded portion (a bent portion 32c) of the second auxiliary band section 32 when viewed in a planar view (refer to FIG. 1(a)) of the body section 10, the other end 52b of the band-shaped member can be engaged with a portion except for the stretchable portion 12d of the protruding section 12 on the left end 10a side of the body section 10 in the front surface of the body section 10, and the second adjustment band section 52 is paired with the first adjustment band section 51.

In particular, one end 52a of the second adjustment band section 52 according to this embodiment is obliquely fixed to the approximately center of the non-stretchable portion 12e of the protruding section 12 on the left end 10a side of the body section 10 in the front surface of the body section 10 in a state where the other end 52b side faces toward the intersection portion of the first auxiliary band section 31 and the second auxiliary band section 32 with the approximately center of the non-stretchable portion 12e of the protruding section 12 on the left end 10a side of the body section 10 in the front surface of the body section 10 as a supporting point, in the flatly-laid state (refer to FIG. 2(a)) in which the engagement of the other end 52b of the second adjustment band section 52 is released.

Further, the fixed position of one end 52a and the engagement position of the other end 52b side of the second adjustment band section 52 are on the left end 10a side of the body section 10 with respect to the position (the bent portion 32c) farthest from one end 32a and the other end 32b of the second auxiliary band section 32, in the range of motion of the second ring 42 which is bound to the second auxiliary band section 32 having the natural length in the flatly-laid state (refer to FIG. 1(a)) of the supporter 100.

In the second adjustment band section 52 according to this embodiment, a PP tape which is woven using a polypropylene yarn and a polyester yarn by a needle loom is used as a base material, and one end 52a of the second adjustment band section 52 (the base material) is sandwiched between the stretchable portion 12d (the power net fabric 12c) and the non-stretchable portion 12e (the double raschel knitted fabric 15) of the protruding section 12 at the approximately center in the short side direction S of the protruding section 12 and one end 52a is sewn at the same time as the sewing of the stretchable portion 12d (the power net fabric 12c) and the non-stretchable portion 12e (the double raschel knitted fabric 15) of the protruding section 12.

Further, in the second adjustment band section 52 according to this embodiment, hooks 22c (refer to FIG. 2(a)) of a hook-and-loop fastener, which is engaged with the loops 21 of the hook-and-loop fastener on the left end 10a side of the body section 10, is disposed to be sewn to the surface facing the loops 21 of the hook-and-loop fastener on the left end 10a side of the body section 10, in the other end 52b of the second adjustment band section 52 (the base material).

Further, in the second adjustment band section 52 according to this embodiment, an end portion of the base material, which becomes the other end 52b, is folded back (a folded structure), and the hooks 22c of the hook-and-loop fastener is sewn to be superimposed on the folded-back portion (the folded structure), whereby the thickness of the other end 52b becomes thicker, and thus falling-off of the second adjustment band section 52 from the second ring 42 is prevented and a wearer can easily grip the other end 52b. Therefore, it is possible to obtain an easy-to-use supporters 100.

In particular, in the supporter 100 according to this embodiment, the natural length of the first auxiliary band section 31 is longer than the distance between one end of the upper side 11a (the upper end of the left side 11c) of the back-contact section 11 and the approximately center of the other side (the right side 11d) of the lateral sides of the back-contact section 11, and the natural length of the second auxiliary band section 32 is longer than the distance between the other end of the upper side 11a (the upper end of the right side 11d) of the back-contact section 11 and the approximately center of one side (the left side 11c) of the lateral sides of the back-contact section 11.

For this reason, in the first auxiliary band section 31, even in a state where the first auxiliary band section 31 does not receive a tensile load from the first adjustment band section 51 (the first ring 41), a bent portion (the bent portion 31c which is engaged with the first ring 41) is formed, and in a case where the supporter 100 is worn and the first adjustment band section 51 is forced forward, the extension direction of the first auxiliary band section 31 is specified, and extension starting resistance of the first auxiliary band section 31 is small, and thus the first adjustment band section 51 can be smoothly forced.

Similarly, in the second auxiliary band section 32, even in a relaxed state, a bent portion (the bent portion 32c which is engaged with the second ring 42) is formed, and in a case where the supporter 100 is worn and the second adjustment band section 52 is forced forward, the extension direction of the second auxiliary band section 32 is specified, and extension starting resistance of the second auxiliary band section 32 is small, and thus the second adjustment band section 52 can be smoothly forced.

The support band section 70 according to this embodiment is composed of a band-shaped member having stretchability in the longitudinal direction and is fixed to the vicinity of the lower side 11b of the back-contact section 11 between the intersection portion of the first auxiliary band section 31 and the second auxiliary band section 32 and the lower side 11b of the back-contact section 11, and hooks 22d of a hook-and-loop fastener are disposed at both end portions.

That is, the support band section 70 is disposed at a position which does not overlap the intersection portion of the first auxiliary band section 31 and the second auxiliary band section 32, on the back-contact section 11.

Further, the supporter 100 according to this embodiment is provided with an annular first guide part 71 which is disposed in the vicinity of a lower end of each of both lateral sides (the left side 11c and the right side 11d) of the back-contact section 11, and into which the support band section 70 is inserted.

In the support band section 70 according to this embodiment, a rubber weave which is woven using a polyurethane yarn and a polyester yarn by a needle loom is used as a base material, similarly to the first auxiliary band section 31 and the second auxiliary band section 32.

Further, in the support band section 70 according to this embodiment, the hooks 22d of the hook-and-loop fasteners (refer to FIG. 2(a)), which are engaged with the loops 21 of the hook-and-loop fasteners of the body section 10, are disposed to be sewn to the surfaces facing the loops 21 of the hook-and-loop fasteners of the body section 10, in both ends (a left end 70a and a right end 70b) of the support band section (the base material).

Further, in the first guide part 71 according to this embodiment, a grosgrain tape is used, and a piece of grosgrain tape is bent in half and both ends of the bent grosgrain tape are gripped along with the edges of the back-contact section 11, the protruding section 12, and the grosgrain tape 13 by the binder tape 14 and sewn. Further, the first guide part 71 is disposed so as to conform to the grosgrain tape 13, and a bent portion of the grosgrain tape is sewn to the body section (the grosgrain tape 13, the raschel mesh 11f, the crochet-knitted fabric 11g, and the power net fabric 12c).

The support band section 70 according to this embodiment has a configuration in which a single band-shaped member is used as a base material, a central portion of the band-shaped member is fixed to the back-contact section 11 by being sewn to the vicinity of the center of the lower side 11b of the back-contact section 11 (by a seam 70c), and hooks 22d are disposed at both ends (the left end 70a and the right end 70b). However, a configuration is also acceptable in which two band-shaped members having the same length, width, and rate of elongation are used as base materials, one end of each band-shaped member is fixed to the back-contact section 11 by being sewn to the vicinity of the center of the lower side 11b of the back-contact section 11, and the hooks 22d is disposed at the other end of each band-shaped member.

Further, the support band section 70 according to this embodiment is disposed on the lower side 12b side of the protruding section 12 with respect to the first ring 41 and the second ring 42, as shown in FIG. 6(d).

In this way, in a case where the supporter 100 is worn, the first ring 41 and the second ring 42 do not interfere with the support band section 70, and therefore, the movements of the first ring 41 and the second ring 42 associated with the motions of a wearer are not inhibited. That is, in the supporter 100 according to this embodiment, the length (expansion and contraction) between the bent portion 31c (the bent portion 32c) and one end 31a (one end 32a) and the length (expansion and contraction) between the bent portion 31c (the bent portion 32c) and the other end 31b (the other end 32b) in the first auxiliary band section 31 (the second auxiliary band section 32) can be adjusted in accordance with the motions of a wearer by the slide of the first ring 41 and the second ring 42, and thus it is possible to prevent occurrence of wrinkles of the first auxiliary band section 31 (the second auxiliary band section 32).

Further, the support band section 70 does not interfere with the first ring 41 and the second ring 42, and therefore, when the supporter 100 is worn, in a case where the first adjustment band section 51 and the second adjustment band section 52 are engaged with the body section 10 after the support band section 70 is engaged with the body section 10, an operation and effect in which it is possible to smoothly slide the first ring 41 and the second ring 42 without inhibiting the movements of the first ring 41 and the second ring 42 associated with the motion of forcing the first adjustment band section 51 and the second adjustment band section 52 forward are exhibited.

Further, the support band section 70 according to this embodiment overlaps only a portion of each of the other ends 31b and 32b of the first auxiliary band section 31 and the second auxiliary band section 32 when viewed in a planar view (refer to FIG. 1(a)) of the body section 10, whereby the support band section 70 does not interfere with the first ring 41 and the second ring 42, and in a case where the supporter 100 is worn, the support band section 70 presses the other ends 31b and 32b of the first auxiliary band section 31 and the second auxiliary band section 32, and thus it is possible to prevent turn-up of the first auxiliary band section 31 and the second auxiliary band section 32 in the vicinity of the other ends 31b and 32b.

Further, the support band section 70 according to this embodiment overlaps only a portion of each of one ends 51a and 52a of the first adjustment band section 51 and the second adjustment band section 52 when viewed in a planar view (refer to FIG. 1(a)) of the body section 10, whereby the support band section 70 does not interfere with the first ring 41 and the second ring 42, and in a case where the supporter 100 is worn, the support band section 70 presses one ends 51a and 52a of the first adjustment band section 51 and the second adjustment band section 52, and thus it is possible to prevent turn-up of the first adjustment band section 51 and the second adjustment band section 52 in the vicinity of one ends 51a and 52a.

Next, an operation and effects due to the supporter 100 being provided with the first auxiliary band section 31 and the second auxiliary band section 32, the first ring 41 and the second ring 42, the first adjustment band section 51 and the second adjustment band section 52, and the support band section 70 will be described along with the procedure of wearing the supporter 100 by using FIGS. 3, 4, and 5.

First, a wearer inserts the pressing section 60 into the back-contact section 11 through the opening 11e and creates a state where the engagement of the hooks 22b of the first adjustment band section 51 with the loops 21 on the right end 10b side of the body section 10 (the protruding section 12) is released, the engagement of the hooks 22c of the second adjustment band section 52 with the loops 21 on the left end 10a side of the body section 10 (the protruding section 12) is released, and the engagement of the hooks 22d on the sides of both ends (the left end 70a and the right end 70b) of the support band section 70 with the loops 21 on the sides of both ends (the left end 10a and the right end 10b) of the body section (the protruding section 12).

Then, the wearer makes the back-contact section 11 of the body section 10 be supported on the back portion (the pelvis) of the wearer, as shown in FIG. 3, and thereafter, in a state where the stretchable portions 12d of the protruding sections 12 are extended to an elongation limit in the longitudinal direction L, the wearer winds the body section 10 around the waist portion of the wearer from the left end 10a side, and then winds the body section 10 around the waist portion of the wearer from the right end 10b side, and makes the hooks 22a on the right end 10b side of the body section 10 (the protruding section 12) be engaged with the loops 21 on the left end 10a side of the body section 10 (the protruding section 12).

In this case, the first auxiliary band section 31 and the second auxiliary band section 32 do not receive the tensile loads from the first adjustment band section 51 (the first ring 41) and the second adjustment band section 52 (the second ring 42), and therefore, the first auxiliary band section 31 and the second auxiliary band section 32 are in a relaxed state (the natural length) and do not press the back-contact section 11.

Then, the wearer grips each of the other end 51b of the first adjustment band section 51 and the other end 52b of the second adjustment band section 52 with one hand and forces the first adjustment band section 51 and the second adjustment band section 52 forward.

In this case, the first ring 41 slides on the first adjustment band section 51 to follow the movement of the other end 51b of the first adjustment band section 51 and moves forward due to the first auxiliary band section 31 having stretchability, and the first auxiliary band section 31 extends to follow the movement of the first ring 41.

Similarly, the second ring 42 slides on the second adjustment band section 52 to follow the movement of the other end 52b of the second adjustment band section 52 and moves forward due to the second auxiliary band section 32 having stretchability, and the second auxiliary band section 32 extends to follow the movement of the second ring 42.

Further, a force acts on the stretchable portions 12d of the protruding sections 12 in a direction of narrowing the distance between the back-contact section 11 (the grosgrain tape 13) and the hook-and-loop fastener (the loops 21), by the first auxiliary band section 31, the first ring 41, and the first adjustment band section 51, and the second auxiliary band section 32, the second ring 42, and the second adjustment band section 52.

However, in the supporter 100 according to this embodiment, the hooks 22a on the right end 10b side of the body section 10 is engaged with the loops 21 on the left end 10a side of the body section 10 in a state where the stretchable portion 12d having stretchability higher than the stretchability of the first auxiliary band section 31 and the second auxiliary band section 32 is extended to the elongation limit in the longitudinal direction L, and therefore, before the extended stretchable portion 12d begins to contract, the first auxiliary band section 31 and the second auxiliary band section 32 begin to extend, and thus it is possible to narrow the distance between the back-contact section 11 and the loops by an amount corresponding to the elongation of the stretchable portion 12d and it is possible to suppress occurrence of wrinkles in the stretchable portion 12d.

In the first auxiliary band section 31, if the elongation of the band-shaped member between the bent portion 31c and the other end 31b reaches a limit value, the first ring 41 is moved upward, and the band-shaped member between the bent portion 31c and one end 31a is sent to the other end 31b side, and thus the band-shaped member on the one end 31a side and the band-shaped member on the other end 31b side complement to each other.

Similarly, in the second auxiliary band section 32, if the elongation of the band-shaped member between the bent portion 32c and the other end 32b reaches a limit value, the second ring 42 is moved upward, and the band-shaped member between the bent portion 32c and one end 32a is sent to the other end 32b side, and thus the band-shaped member on the one end 32a side and the band-shaped member on the other end 32b side complement to each other.

Then, as shown in FIG. 4, at a stage in which a desired tightening feeling with respect to the waist portion has been obtained, the wearer makes the hooks 22b of the first adjustment band section 51 be engaged with the loops 21 on the right end 10b side of the body section 10 (the protruding section 12) and makes the hooks 22c of the second adjustment band section 52 be engaged with the loops 21 on the left end 10a side of the body section 10 (the protruding section 12).

In this case, the first auxiliary band section 31 and the second auxiliary band section 32 receive the tensile loads from the first adjustment band section 51 (the first ring 41) and the second adjustment band section 52 (the second ring 42), and therefore, the first auxiliary band section 31 and the second auxiliary band section 32 are in a tension state, and the first auxiliary band section 31 and the second auxiliary band section 32 intersect one another in the vicinity of the upper side 11a of the back-contact section 11 due to three-point support of one end (31a or 32a), the other end (31b or 32b), and the bent portion (31c or 32c), whereby the vicinity of the upper side 11a of the back-contact section 11 is pressed by the entirety of the first auxiliary band section 31 and the second auxiliary band section 32.

Finally, as shown in FIG. 5, the wearer grips each of the left end 70a and the left end 70b of the support band section 70 with one hand and forces the support band section 70 forward, and at a stage in which a desired tightening feeling with respect to the waist portion has been obtained, the wearer makes the hooks 22d on the right end 70b side of the support band section 70 be engaged with the loops 21 of the right end 10b side of the body section 10 (the protruding section 12) and makes the hooks 22c on the left end 70a side of the support band section 70 be engaged with the loops 21 of the left end 10a side of the body section 10 (the protruding section 12).

In this case, the support band section 70 is in a tension state and presses the vicinity of the lower side 11b of the back-contact section 11.

The procedure of wearing the supporter 100 described above has been described with respect to a case where after the first adjustment band section 51 and the second adjustment band section 52 are engaged with the body section 10 (the protruding sections 12), the support band section 70 is engaged with the body section 10 (the protruding sections 12). However, the first adjustment band section 51 and the second adjustment band section 52 may be engaged with the body section 10 (the protruding sections 12) after the support band section 70 is engaged with the body section 10 (the protruding sections 12).

As described above, in the supporter 100 according to this embodiment, the support band section 70 can compensate for a decrease in the ratio of the pressing force by the first auxiliary band section 31 and the second auxiliary band section 32 against the back-contact section 11 due to making the width of the back-contact section 11 wider than the width of a back-contact section of a supporter of the related art.

Further, in the supporter 100 according to this embodiment, the floating of the supporter 100 from the back portion of a wearer in the upper side 11a and the lower side 11b of the back-contact section 11 is prevented by the pressing forces of the intersection portion of the first auxiliary band section 31 and the second auxiliary band section 32 and the support band section 70 against the back-contact section 11, and thus it is possible to support the entire waist portion of the wearer.

That is, in the supporter 100 according to this embodiment, a strongest pressing force $F_A$ of the vicinity of the upper side 11a of the back-contact section 11 by the intersection portion of the first auxiliary band section 31 and the second auxiliary band section 32, a weak pressing force $F_B$ of the center of the back-contact section 11 by the tensile loads from the other end 31b of the first auxiliary band section 31 and the other end 32b of the second auxiliary band section 32, and a strong pressing force $F_C$ of the vicinity of the lower side 11b of the back-contact section 11 by the support band section 70 can be applied to the back-contact section 11 ($F_A > F_C > F_B$). In this way, in the supporter 100 according to this embodiment, the floating from the back portion of a wearer in the vicinity of the upper side 11a and the lower side 11b of the back-contact section 11 is prevented, and the entire waist portion of the wearer can be supported with an appropriate pressing force to correspond to the curved surface of the waist portion of the wearer. Further, in the supporter 100 according to this embodiment, the intersection portion of the first auxiliary band section 31 and the second auxiliary band section 32 is disposed in the vicinity of the upper side 11a of the back-contact section 11, whereby the intersection portion of the first auxiliary band section 31 and the second auxiliary band section 32 is located in the vicinity of the first lumbar vertebra and the second lumbar vertebra of a wearer, and therefore, it is possible to alleviate a lumbago such as a herniated disc by supporting the vicinity of the first lumbar vertebra and the second lumbar vertebra of the wearer.

In the supporter 100 according to this embodiment, as long as it is possible to apply different pressing forces ($F_A > F_C > F_B$) to the vicinity (a region A) of the upper side 11a, the center (a region B), and the vicinity (a region C) of the lower side 11b of the back-contact section 11, as shown in FIG. 7(b), a configuration is also acceptable in which the support band section 70 does not overlap the other ends 31b and 32b of the first auxiliary band section 31 and the second auxiliary band section 32 and one ends 51a and 52a of the first adjustment band section 51 and the second adjustment band section 52, as shown in FIG. 7(a).

Further, the supporter 100 according to this embodiment has been described with respect to a case where the protruding sections 12 protrude upward from both sides of the back-contact section 11, as shown in FIGS. 1(a) and 7(a). However, a supporter 100 is also acceptable in which the protruding sections 12 protrude downward from both sides of the back-contact section 11, as shown in FIG. 8, and a supporter 100 is also acceptable in which the protruding sections 12 protrude substantially horizontally from both sides of the back-contact section 11.

Second Embodiment of the Present Invention

FIG. 9(a) is a diagram showing the front surface of a supporter according to a second embodiment, and FIG. 9(b) is a diagram showing the lining surface of the supporter shown in FIG. 9(a). In FIG. 9, the same reference numerals as those in FIG. 1 denote identical or corresponding portions, and the description thereof is omitted.

In the first auxiliary band section 31 and the second auxiliary band section 32 according to the first embodiment described above, one ends 31a and 32a and the other ends 31b and 32b are fixed such that the two band-shaped members intersect one another in the vicinity of the upper side 11a of the back-contact section 11.

In contrast, in the first auxiliary band section 31 and the second auxiliary band section 32 according to this embodiment, one ends 31a and 32a and the other ends 31b and 32b are fixed such that the two band-shaped members intersect one another in the vicinity of the lower side 11b of the back-contact section 11.

Further, the support band section 70 according to this embodiment is fixed to the vicinity of the upper side 11a of the back-contact section 11 between the intersection portion of the first auxiliary band section 31 and the second auxiliary band section 32 and the upper side 11a of the back-contact section 11.

That is, also in this embodiment, the support band section 70 is disposed at a position which does not overlap the intersection portion of the first auxiliary band section 31 and the second auxiliary band section 32, on the back-contact section 11.

Further, the support band section 70 according to this embodiment is disposed on the upper side 12a side of the protruding section 12 with respect to the first ring 41 and the second ring 42, as shown in FIG. 9(a).

Further, the first guide part 71 according to this embodiment is disposed in the vicinity of the upper end of each of both lateral sides (the left side 11c and the right side 11d) of the back-contact section 11, and the support band section 70 is inserted into the first guide part 71.

Further, in the first auxiliary band section 31 according to this embodiment, one end 31a is fixed to one end of the lower side 11b of the back-contact section 11 and/or a lower end of one side (for example, the left side 11c) of the lateral sides of the back-contact section 11 in the front surface of the body section 10, the first auxiliary band section 31 is folded back on the outside (the right side) of the back-contact section 11 when viewed in a planar view (refer to FIG. 9(a)) of the body section 10, and the other end 31b of the band-shaped member is fixed to the approximately center in the vicinity of the other side (for example, the right side 11d) of the lateral sides being in contact with the back-contact section 11 in the stretchable portion 12d of the protruding section 12 in the front surface of the body section 10.

Further, in the second auxiliary band section 32 according to this embodiment, one end 32a is fixed to the other end of the lower side 11b of the back-contact section 11 and/or a lower end of the other side (for example, the right side 11d) of the lateral sides of the back-contact section 11 in the front surface of the body section 10, the second auxiliary band section 32 is folded back on the outside (the left side) of the back-contact section 11 when viewed in a planar view (refer to FIG. 9(a)) of the body section 10, and the other end 32b of the band-shaped member is fixed to the approximately center in the vicinity of one side (for example, the left side 11c) of the lateral sides being in contact with the back-contact section 11 in the stretchable portion 12d of the protruding section 12 in the front surface of the body section 10.

Meanwhile, as long as the first auxiliary band section 31 and the second auxiliary band section 32 intersect one another in the vicinity of the lower side 11b of the back-contact section 11, both ends (one end 31a and the other end 31b) of the first auxiliary band section 31 and both ends (one end 32a and the other end 32b) of the second auxiliary band section 32 are not limited to the fixed positions shown in FIG. 9(a).

As described above, in the supporter 100 according to this embodiment, a strongest pressing force $F_C$, of the vicinity (the region C, refer to FIG. 7(b)) of the lower side 11b of the back-contact section 11 by the intersection portion of the first auxiliary band section 31 and the second auxiliary band section 32, a weak pressing force $F_B$ of the center (the region B, refer to FIG. 7(b)) of the back-contact section 11 by the tensile loads from the other end 31b of the first auxiliary band section 31 and the other end 32b of the second auxiliary band section 32, and a strong pressing force $F_A$ of the vicinity (the region A, refer to FIG. 7(b)) of the upper side 11a of the back-contact section 11 by the support band section 70 can be applied to the back-contact section 11 ($F_C > F_A > F_B$). In this way, in the supporter 100 according to this embodiment, the floating from the back portion of a wearer in the vicinity of the upper side 11a and the lower side 11b of the back-contact section 11 is prevented, and thus the entire waist portion of the wearer can be supported with an appropriate pressing force to correspond to the curved surface of the waist portion of the wearer. Further, in the supporter 100 according to this embodiment, the intersection portion of the first auxiliary band section 31 and the second auxiliary band section 32 is disposed in the vicinity of the lower side 11b of the back-contact section 11, whereby the intersection portion of the first auxiliary band section 31 and the second auxiliary band section 32 is located in the vicinity of the sacroiliac joint of a wearer, and therefore, it is possible to limit the movement of the sacroiliac joint and stabilize the sacroiliac joint.

Further, the supporter 100 according to this embodiment has been described with respect to a case where the protruding sections 12 protrude upward from both sides of the back-contact section 11, as shown in FIG. 9. However, similar to the first embodiment, a supporter 100 is also acceptable in which the protruding sections 12 protrude downward from both sides of the back-contact section 11, and a supporter 100 is also acceptable in which the protruding sections 12 protrude substantially horizontally from both sides of the back-contact section 11.

Third Embodiment of the Present Invention

FIG. 10(a) is a diagram showing the front surface of a supporter according to a third embodiment, and FIG. 10(b) is a diagram showing the front surface of another supporter according to the third embodiment. In FIG. 10, the same reference numerals as those in FIG. 1 denote identical or corresponding portions, and the description thereof is omitted.

The supporter 100 according to this embodiment is provided with annular second guide parts 53 which are respectively disposed at the stretchable portions 12d of the right and left protruding sections 12 and into which the first adjustment band section 51 and the second adjustment band section 52 are respectively inserted, as shown in FIG. 10(a).

In the second guide part 53 according to this embodiment, a tape such as the same grosgrain tape as the first guide part 71 or a knitted tape which is knitted using a polyester yarn is used, and the second guide part 53 is disposed by sewing an upper end and a lower end onto the stretchable portion 12d (the power net fabric 12c) in the front surface of the supporter 100.

In this manner, the supporter 100 according to this embodiment is provided with the second guide part 53, whereby it is possible to position each of the first adjustment band section 51 and the second adjustment band section 52, thereby suppressing the traction thereof in an unnecessary direction, and prevent the twist of the first auxiliary band section 31 and the second auxiliary band section 32.

In particular, in the first adjustment band section 51 (the second adjustment band section 52), by making the width of the other end 51b (the other end 52b) wider than the width between upper and lower sewn portions of the second guide part 53, it is possible to prevent falling-out of the first adjustment band section 51 (the second adjustment band section 52) from the second guide part 53.

In the second guide part 53 according to this embodiment, a tape having a length which crosses only the first adjustment band section 51 (the second adjustment band section 52) is used, as shown in FIG. 10(a). However, there is no limitation to this length, and for example, as shown in FIG. 10(b), a tape having a length which crosses the stretchable portion 12d may be used. In this case, both ends of the tape are gripped along with edges of the stretchable portion 12d by the binder tape 14 and sewn, and the tape is sewn to the stretchable portion 12d in the vicinity of the lateral sides of the first adjustment band section 51 (the second adjustment band section 52).

REFERENCE SIGNS LIST

10: body section
10a: left end
10b: right end
11: back-contact section
11a: upper side
11b: lower side
11c: left side
11d: right side
11e: opening
11f: raschel mesh
11g: crochet-knitted fabric
12: protruding section
12a: upper side
12b: lower side
12c: power net fabric
12d: stretchable portion
12e: non-stretchable portion
13: grosgrain tape
14: binder tape
15: double raschel knitted fabric
15a: front knitted surface
15b: back knitted surface
15c: connection portion
21: loops
22a, 22b, 22c, 22d: hooks
31: first auxiliary band section
31a: one end
31b: the other end
31c: bent portion
32: second auxiliary band section
32a: one end
32b: the other end
32c: bent portion
41: first ring
41a: first long hole
41b: second long hole
42: second ring
42a: first long hole
42b: second long hole
51: first adjustment band section
51a: one end
51b: the other end
52: second adjustment band section
52a: one end
52b: the other end
53: second guide part
60: pressing section
61: upper bottom
62: lower bottom
63: concave portion
70: support band section
70a: left end
70b: right end
70c: seam
71: first guide part
100: supporter

The invention claimed is:

1. A band-shaped supporter, comprising:
a back-contact section configured to be brought into contact with a back portion of a wearer;
a plurality of protruding sections which are disposed on both sides of the back-contact section, respectively, and in each of which a stretchable portion having stretchability in a longitudinal direction is disposed in contact with the back-contact section;
a pair of auxiliary band sections which includes two band-shaped members having stretchability in a longitudinal direction such that the two band-shaped members are fixed at ends and intersect one another on the back-contact section, and that a pair of annular rings are slidably disposed at the band-shaped members, respectively;

a pair of adjustment band sections which includes two band-shaped members having stretchability lower than the stretchability of the pair of auxiliary band sections such that each of the two band-shaped members in the pair of adjustment band sections is loosely inserted into a respective one of the annular rings in the pair of auxiliary band sections, and has one end fixed to a portion except for the stretchable portion of each of the plurality of protruding sections and hooks of a hook-and-loop fastener disposed at the opposite end; and a band-shaped support band section which includes a band-shaped member having stretchability in a longitudinal direction and is fixed to the back-contact section such that the band-shaped member of the band-shaped support band section does not overlap an intersection portion of the two band-shaped members of the pair of auxiliary band sections on the back-contact section, and hooks of a hook-and-loop fastener are disposed at opposing end portions of the band-shaped member of the band-shaped support band section.

2. The band-shaped supporter according to claim 1, wherein the pair of auxiliary band sections has both ends fixed such that the pair of auxiliary band sections intersect one another in the vicinity of an upper side of the back-contact section, and the support band section is fixed in the vicinity of a lower side of the back-contact section.

3. The band-shaped supporter according to claim 2, further comprising:
a plurality of annular guide parts formed at lateral sides of the back-contact section such that the support band section is inserted through the annular guide parts.

4. The band-shaped supporter according to claim 3, further comprising:
a plurality of loops of hook-and-loop fasteners of double raschel knitted fabrics formed at end portions of the plurality of protruding sections respectively such that the hooks of the hook-and-loop fasteners of the pair of adjustment band sections and the support band section are engaged.

5. The band-shaped supporter according to claim 2, further comprising:
a plurality of loops of hook-and-loop fasteners of double raschel knitted fabrics formed at end portions of the plurality of protruding sections respectively such that the hooks of the hook-and-loop fasteners of the pair of adjustment band sections and the support band section are engaged.

6. The band-shaped supporter according to claim 1, wherein the pair of auxiliary band sections has both ends fixed such that the pair of auxiliary band sections intersect one another in the vicinity of a lower side of the back-contact section, and the support band section is fixed in the vicinity of an upper side of the back-contact section.

7. The band-shaped supporter according to claim 6, further comprising:
a plurality of annular guide parts formed at lateral sides of the back-contact section such that the support band section is inserted through the annular guide parts.

8. The band-shaped supporter according to claim 7, further comprising:
a plurality of loops of hook-and-loop fasteners of double raschel knitted fabrics formed at end portions of the plurality of protruding sections respectively such that the hooks of the hook-and-loop fasteners of the pair of adjustment band sections and the support band section are engaged.

9. The band-shaped supporter according to claim 6, further comprising:
a plurality of loops of hook-and-loop fasteners of double raschel knitted fabrics formed at end portions of the plurality of protruding sections respectively such that the hooks of the hook-and-loop fasteners of the pair of adjustment band sections and the support band section are engaged.

10. The band-shaped supporter according to claim 1, further comprising:
a plurality of annular guide parts formed at lateral sides of the back-contact section such that the support band section is inserted through the annular guide parts.

11. The band-shaped supporter according to claim 10, further comprising:
a plurality of loops of hook-and-loop fasteners of double raschel knitted fabrics formed at end portions of the plurality of protruding sections respectively such that the hooks of the hook-and-loop fasteners of the pair of adjustment band sections and the support band section are engaged.

12. The band-shaped supporter according to claim 1, further comprising:
a plurality of loops of hook-and-loop fasteners of double raschel knitted fabrics formed at end portions of the plurality of protruding sections respectively such that the hooks of the hook-and-loop fasteners of the pair of adjustment band sections and the support band section are engaged.

13. The band-shaped supporter according to claim 1, wherein the back-contact section comprises a bag body and a plate body inserted in the bag body.

14. The band-shaped supporter according to claim 1, wherein each of the plurality of protruding sections has a stretchable portion comprising a power net fabric and a non-stretchable portion comprising a double raschel knitted fabric such that the stretchable portion is fixed to a respective one of the sides of the back-contact section and the non-stretchable portion formed adjacent to the stretchable portion.

15. The band-shaped supporter according to claim 1, wherein each of the band-shaped members of the pair of auxiliary band sections comprises a base material comprising a rubber weave, and the band-shaped member of the support band section comprises a base material comprising a rubber weave.

16. A band-shaped supporter, comprising:
a back-contact section comprising a bag body and a plate body inserted in the bag body such that the back-contact section has opposing sides and is configured to be brought into contact with a back portion of a wearer;

a plurality of protruding sections each comprising a stretchable portion comprising a power net fabric and a non-stretchable portion comprising a double raschel knitted fabric such that the stretchable portion has stretchability in a longitudinal direction and that the stretchable portion is fixed to a respective one of the opposing sides of the back-contact section and the non-stretchable portion formed adjacent to the stretchable portion;

a pair of auxiliary band sections comprising a pair of band-shaped members having stretchability in a longitudinal direction such that the pair of auxiliary band sections have ends fixed in the back-contact section and the plurality of protruding sections and intersect one another on the back-contact section, and a pair of annular rings slidably provided on the band-shaped members, respectively;

a pair of adjustment band sections comprising a pair of band-shaped members having stretchability lower than the stretchability of the band-shaped members of the pair of auxiliary band sections and loosely inserted into the annular rings in the pair of auxiliary band sections respectively such that each of the pair of adjustment band sections is fixed to the non-stretchable portion of a respective one of the plurality of protruding portions at one end and has hooks of a hook-and-loop fastener at the opposite end; and a band-shaped support band section comprising a band-shaped member fixed to the back-contact section such that the band-shaped member of the band-shaped support band section does not overlap an intersection portion of the two band-shaped members of the pair of auxiliary band sections on the back-contact section, comprises a base material comprising a rubber weave and has stretchability in a longitudinal direction and that the band-shaped member of the band-shaped support band section has hooks of a hook-and-loop fastener at end portions.

17. The band-shaped supporter according to claim 16, wherein the pair of auxiliary band sections has both ends fixed such that the pair of auxiliary band sections intersect one another in the vicinity of an upper side of the back-contact section, and the support band section is fixed in the vicinity of a lower side of the back-contact section.

18. The band-shaped supporter according to claim 16, wherein the pair of auxiliary band sections has both ends fixed such that the pair of auxiliary band sections intersect one another in the vicinity of a lower side of the back-contact section, and the support band section is fixed in the vicinity of an upper side of the back-contact section.

19. The band-shaped supporter according to claim 16, further comprising:

a plurality of annular guide parts formed at lateral sides of the back-contact section such that the support band section is inserted through the annular guide parts.

20. The band-shaped supporter according to claim 16, further comprising:

a plurality of loops of hook-and-loop fasteners of double raschel knitted fabrics formed at end portions of the plurality of protruding sections respectively such that the hooks of the hook-and-loop fasteners of the pair of adjustment band sections and the support band section are engaged.

* * * * *